US010766837B2

(12) United States Patent
Deur-Bert et al.

(10) Patent No.: US 10,766,837 B2
(45) Date of Patent: Sep. 8, 2020

(54) METHOD FOR THE PRODUCTION AND PURIFICATION OF 2,3,3,3-TETRAFLUOROPROPENE

(71) Applicant: Arkema France, Colombes (FR)

(72) Inventors: Dominique Deur-Bert, Charly (FR); Anne Pigamo, Francheville (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/606,783

(22) PCT Filed: Apr. 20, 2018

(86) PCT No.: PCT/FR2018/050995
§ 371 (c)(1),
(2) Date: Oct. 21, 2019

(87) PCT Pub. No.: WO2018/197788
PCT Pub. Date: Nov. 1, 2018

(65) Prior Publication Data
US 2020/0157024 A1 May 21, 2020

(30) Foreign Application Priority Data
Apr. 28, 2017 (FR) ...................... 17 53744

(51) Int. Cl.
*C07C 17/20* (2006.01)
*C07C 17/383* (2006.01)
(52) U.S. Cl.
CPC .......... *C07C 17/206* (2013.01); *C07C 17/383* (2013.01)
(58) Field of Classification Search
CPC ... C07C 17/383; C07C 17/206; C07C 17/275; C07C 17/25; C07C 21/18; C07C 17/38
See application file for complete search history.

(56) References Cited

U.S. PATENT DOCUMENTS

2011/0160499 A1  6/2011  Wendlinger et al.
2019/0127303 A1* 5/2019  Ondrus ............... C07C 17/275

FOREIGN PATENT DOCUMENTS

EP    939071 A1    9/1999
WO    9819982 A1   5/1998
(Continued)

OTHER PUBLICATIONS

ISA/EP; International Search Report and Written Opinion for International Patent Application No. PCT/FR2018/050995 dated Jul. 27, 2018.

*Primary Examiner* — Jafar F Parsa
(74) *Attorney, Agent, or Firm* — NK Patent Law

(57) ABSTRACT

The invention refers to a process for the production of 2,3,3,3-tetrafluoropropene carried out starting from a starting composition comprising the stages of bringing the starting composition into contact, in the presence of a catalyst, with HF in order to produce a composition A comprising 2,3,3,3-tetrafluoropropene (HFO-1234yf), intermediate products B consisting of 2-chloro-3,3,3-trifluoropropene (HCFO-1233xf), 1,1,1,2,2-pentafluoropropane (HFC-245cb), and byproducts C consisting of E-1-chloro-3,3,3-trifluoro-1-propene (HCFO-1233zdE), trans-1,3,3,3-tetrafluoro-1-propene (HFO-1234zeE) and 1,1,1,3,3-pentafluoropropane (HFC-245fa); recovery of said composition A and purification of the latter in order to form and recover a first gas stream G1 comprising HCl, 2,3,3,3-tetrafluoropropene (HFO-1234yf), a part of the unreacted HF, a part of the intermediate products B and a part of the byproducts C; and a stream, which is preferably liquid, L1 comprising a part of the unreacted HF, a part of the intermediate products B and a part of the byproducts C.

15 Claims, 5 Drawing Sheets

(56) References Cited

FOREIGN PATENT DOCUMENTS

| WO | 03068716 | A1 | 8/2003 |
| WO | 2007079431 | A2 | 7/2007 |
| WO | 2008040969 | A2 | 4/2008 |
| WO | 2008054781 | A1 | 5/2008 |
| WO | 2009118628 | A1 | 10/2009 |
| WO | 2013088195 | A1 | 6/2013 |

* cited by examiner

US 10,766,837 B2

METHOD FOR THE PRODUCTION AND PURIFICATION OF 2,3,3,3-TETRAFLUOROPROPENE

CROSS-REFERENCE TO RELATED APPLICATIONS

This application is a U.S. National Stage application of International Patent Application No. PCT/FR2018/050995, filed on Apr. 20, 2018, which claims the benefit of French Patent Application No. 1753744, filed on Apr. 28, 2017.

TECHNICAL FIELD OF THE INVENTION

The invention relates to a process for the purification of 2,3,3,3-tetrafluoro-1-propene. In addition, the invention also relates to a process for the production and purification of 2,3,3,3-tetrafluoro-1-propene.

TECHNOLOGICAL BACKGROUND OF THE INVENTION

Hydrofluorocarbons (HFCs) and in particular hydrofluoroolefins (HFOs), such as 2,3,3,3-tetrafluoro-1-propene (HFO-1234yf), are compounds known for their properties of refrigerants and heat-exchange fluids, extinguishers, propellants, foaming agents, blowing agents, gaseous dielectrics, polymerization medium or monomer, support fluids, agents for abrasives, drying agents and fluids for energy production units.

HFOs have been identified as desirable alternatives to HCFC as a result of their low ODP (ozone depletion potential) and GWP (global warming potential) values.

Most of the processes for the manufacture of hydrofluoroolefins involve a fluorination and/or dehydrohalogenation reaction. This type of reaction is carried out in the gas phase and generates impurities which consequently have to be removed in order to obtain the desired compound in a sufficient degree of purity for the applications targeted.

For example, in the context of the production of 2,3,3,3-tetrafluoro-1-propene (HFO-1234yf), the presence of impurities, such as 1-chloro-3,3,3-trifluoro-1-propene (HCFO-1233zd), 1,3,3,3-tetrafluoro-1-propene (HFO-1234ze) and 1,1,1,3,3-pentafluoropropane (HFC-245fa), is observed. These impurities are isomers of the main compounds targeted at being obtained by the process for the production of 2,3,3,3-tetrafluoro-1-propene, besides the latter, i.e. 2-chloro-3,3,3-trifluoro-1-propene (HCFO-1233xf) and 1,1,1,2,2-pentafluoropropane (HFC-245cb). In view of the respective boiling points of 1-chloro-3,3,3-trifluoro-1-propene (HCFO-1233zd), 1,3,3,3-tetrafluoro-1-propene (HFO-1234ze) and 1,1,1,3,3-pentafluoropropane (HFC-245fa), these can accumulate in the reaction loop and thus prevent the formation of the products of interest.

The purification of this type of reaction mixture can be carried out by various techniques known from the prior art, such as, for example, distillation. However, when the compounds to be purified have boiling points which are too close or when these form azeotropic or quasi-azeotropic compositions, distillation is not an effective process. Extractive distillation processes have thus been described.

EP 0 864 554 discloses a process for the purification of a mixture comprising 1,1,1,3,3-pentafluoropropane (HFC-245fa) and trans-1-chloro-3,3,3-trifluoro-1-propene (HCFO-1233zd) by distillation in the presence of a solvent having a boiling point which is greater than that of trans-1-chloro-3,3,3-trifluoro-1-propene.

WO 03/068716 discloses a process for the recovery of pentafluoroethane from a mixture comprising pentafluoroethane and chloropentafluoroethane by distillation in the presence of hexafluoropropene.

Also, WO 98/19982 discloses a process for the purification of 1,1-difluoroethane by extractive distillation. The process consists in bringing an extraction agent into contact with a mixture of 1,1-difluoroethane and vinyl chloride. The extraction agent is chosen from hydrocarbons, alcohols and chlorocarbons having a boiling point of between 10° C. and 120° C. As mentioned by WO 98/19982, the selection of the extraction agent can prove to be complex depending on the products to be separated. WO 2013/088195 discloses a process for the preparation of 2,3,3,3-tetrafluoropropene from 1,1,1,2,3-pentachloropropane and/or 1,1,2,2,3-pentachloropropane. There thus still exists a need for the implementation of a specific process for the purification of 2,3,3,3-tetrafluoro-1-propene.

SUMMARY OF THE INVENTION

In a process for the production of 2,3,3,3-tetrafluoro-1-propene, the choice of specific operating conditions can promote the presence of certain impurities or of isomers thereof. The presence of impurities, such as 1,3,3,3-tetrafluoro-1-propene (HFO-1234ze), may be observed, as may that of 1-chloro-3,3,3-trifluoro-1-propene (HCFO-1233zd) and 1,1,1,3,3-pentafluoropropane (HFC-245fa). Compounds generating impurities of halogenated propyne type, such as trifluoropropyne, chlorotrifluoropropyne or tetrafluoropropyne, have also been identified. The impurities can originate from side reactions brought about by compounds produced as intermediates during the production of 2,3,3,3-tetrafluoropropene and may exhibit physical properties such that their removal may prove to be complex. Some impurities, such as halogenated propynes, can promote the formation of coke and result in a deactivation of the catalyst. There is thus a need to provide a process which limits the presence of impurities such as halogenated propynes and compounds from which they result. The present invention makes possible in particular the production of 2,3,3,3-tetrafluoro-1-propene with an improved purity.

According to a first aspect, the invention provides a process for the production and purification of 2,3,3,3-tetrafluoropropene (HFO-1234yf) carried out starting from a starting composition comprising at least one compound of formula (I) $CH_{(n+2)}(X)_m$—$CH_p(X)_{(n+1)}$—$CX_{(3+p-m)}$, where X independently represents F or Cl; n, m and p are, independently of one another, 0 or 1 with n+m=0 or 1, n+p=0 or 1 and m−p=0 or 1, at least one X being Cl; said process comprising the stages of:

a) bringing the starting composition into contact, in the presence of a catalyst, with HF under conditions effective in producing a composition A comprising HCl, a part of the unreacted HF, 2,3,3,3-tetrafluoropropene (HFO-1234yf), intermediate products B consisting of 2-chloro-3,3,3-trifluoro-1-propene (HCFO-1233xf), 1,1,1,2,2-pentafluoropropane (HFC-245cb) and trans-1,3,3,3-tetrafluoro-1-propene (HFO-1234zeE) and byproducts C consisting of trans-1-chloro-3,3,3-trifluoro-1-propene (HCFO-1233zdE), cis-1-chloro-3,3,3-trifluoro-1-propene (HCFO-1233zdZ), cis-1,3,3,3-tetrafluoro-1-propene (HFO-1234zeZ), 1,1,1,3,3-pentafluoropropane (HFC-245fa), 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe), 1,1,1,3,3,3- hexafluoropropane (HFC-236fa) and optionally one or more compounds of formula (II) $C_nH_xF_yCl_z$ in which n=4, 5 or 6, x is an integer from 0 to 6, y is an integer from 4 to 12, z is an integer from 0 to 6, with 2n=x+y+z if w is 1 or 2n−2=x+y+z if w is 2 or 2n+2=x+y+z if w=0, w being the number of unsaturations in the compound of formula (II) considered;

b) recovery of said composition A and purification, preferably distillation, of the latter in order to form and recover a gas stream G1 comprising HCl, 2,3,3,3-tetrafluoropropene (HFO-1234yf), a part of the unreacted HF, a part of the intermediate products B and a part of the byproducts C; and a stream, which is preferably liquid, L1 comprising a part of the unreacted HF, a part of the intermediate products B and a part of the byproducts C;

characterized in that said gas stream G1 purified by the following stages:

b1) distillation of the gas stream G1 in order to recover a stream G1a comprising HCl, advantageously at the distillation column top, and a stream G1b comprising 2,3,3,3-tetrafluoropropene (HFO-1234yf), a part of the unreacted HF, said a part of the intermediate products B and said a part of the byproducts C, advantageously at the distillation column bottom;

b2-1) distillation of said stream G1b obtained in stage b1) under conditions effective in forming a gas stream G1c comprising 2,3,3,3-tetrafluoropropene (HFO-1234yf), a portion of said part of said unreacted HF, a portion of said part of the intermediate products B, advantageously at the distillation column top, and a liquid stream G1d comprising a portion of said part of the intermediate products B and said part of the byproducts C and a portion of said part of said unreacted HF, advantageously at the distillation column bottom;

b2-2) distillation of said stream G1d obtained in stage b2-1) under conditions effective in forming a stream G1d' comprising said portion of said part of the intermediate products B, said portion of said part of said unreacted HF and a portion of said part of the byproducts C comprising cis-1,3,3,3-tetrafluoro-1-propene (HFO-1234zeZ), 1,1,1,3,3,3-hexafluoropropane (HFC-236fa) and a part of trans-1-chloro-3,3,3-trifluoro-1-propene (HCFO-1233zdE) and 1,1,1,3,3-pentafluoropropane (HFC-245fa); and a stream G1d'' comprising a portion of said part of the byproducts C comprising cis-1-chloro-3,3,3-trifluoro-1-propene (HCFO-1233zdZ), 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe), and optionally one or more compounds of formula (II) $C_nH_xF_yCl_z$ in which n=4, 5 or 6, x is an integer from 0 to 6, y is an integer from 4 to 12, z is an integer from 0 to 6, with 2n=x+y+z if w is 1 or 2n−2=x+y+z if w is 2 or 2n+2=x+y+z if w is 0, w being the number of unsaturations in the compound of formula (II) considered.

The number of unsaturations corresponds to the number of carbon-carbon double bonds in the compound of formula (II).

According to a preferred embodiment, at least 90% of the 1,1,1,2,2-pentafluoropropane and of the trans-1,3,3,3-tetrafluoro-1-propene contained in the stream G1d are recovered in the stream G1d'; advantageously, at least 91%, preferably at least 92%, more preferably at least 93%, in particular at least 94%, more particularly at least 95%, favorably at least 96%, preferably favorably at least 97%, particularly favorably at least 98%, of the 1,1,1,2,2-pentafluoropropane and of the trans-1,3,3,3-tetrafluoropropene contained in the stream G1d are recovered in the stream G1d'.

According to a preferred embodiment, the stream G1d' comprises from 60% to 70% by weight of 1,1,1,2,2-pentafluoropropane, from 1% to 5% by weight of trans-1,3,3,3-tetrafluoropropene and from 10% to 15% by weight of 2-chloro-3,3,3-trifluoropropene, based on the total weight of the stream G1d'.

According to a preferred embodiment, at least 85% of the cis-1,3,3,3-tetrafluoro-1-propene (HFO-1234zeZ) and of the 1,1,1,3,3,3-hexafluoropropane (HFC-236fa) contained in the stream G1d are recovered in the stream G1d'; advantageously, at least 90%, preferably at least 92%, more preferably at least 93%, in particular at least 95%, more particularly at least 97%, of the cis-1,3,3,3-tetrafluoro-1-propene (HFO-1234zeZ) and of the 1,1,1,3,3,3-hexafluoropropane (HFC-236fa) contained in the stream G1d are recovered in the stream G1d'.

According to a preferred embodiment, the stream G1d' comprises from 0.1% to 0.5% by weight of cis-1,3,3,3-tetrafluoro-1-propene (HFO-1234zeZ), from 1.0% to 5.0% by weight of 1,1,1,3,3,3-hexafluoropropane (HFC-236fa), from 0.5% to 2.0% by weight of trans-1-chloro-3,3,3-trifluoro-1-propene (HCFO-1233zdE) and from 0.1% to 1.0% by weight of 1,1,1,3,3-pentafluoropropane (HFC-245fa), based on the total weight of the stream G1d'.

According to a preferred embodiment, the stream G1d' also comprises 2-chloro-1,1,1,3,3-pentafluoropropane (HCFC-235da), 1,2-dichloro-3,3,3-trifluoropropene (HCFO-1223xd) and 2-chloro-1,3,3,3-tetrafluoropropene (HCFO-1224xe) in a total content of less than 5% by weight, based on the total weight of G1d', advantageously less than 4% by weight, preferably less than 3% by weight, more preferably less than 2% by weight, in particular less than 1% by weight, more particularly less than 0.5% by weight, based on the total weight of G1d'.

According to a preferred embodiment, the stream G1d' is recycled in stage a).

According to a preferred embodiment, the process also comprises the stages:

b3) bringing the stream G1c into contact with an aqueous hydrofluoric acid solution with a concentration of greater than 40% in order to form a two-phase stream G1c' comprising 2,3,3,3-tetrafluoropropene (HFO-1234yf), hydrofluoric acid, a portion of said part of the intermediate products B and a portion of said part of the byproducts C, b4) storage of said two-phase stream G1c' in a holding tank, said second two-phase stream consisting of a liquid phase and of a gas phase, b5) passage of said gas phase of said stream G1c' into an absorption column fed countercurrentwise with an aqueous flow in order to form a stream G1c'' comprising 2,3,3,3-tetrafluoropropene (HFO-1234yf), a portion of said part of the intermediate products B and a portion of said part of the byproducts C and a stream G1c''' comprising HF;

and optionally the stages:

b6) neutralization of said stream G1c'' obtained in stage b5) with an aqueous alkaline solution in order to form a neutralized stream, and b7) drying of said neutralized stream obtained in stage b6), preferably over a molecular sieve, in order to form a neutralized and dried stream G1c''''.

According to a preferred embodiment, the aqueous hydrofluoric acid solution used in stage b3) is at a temperature of between 0 and 30° C. before it is brought into contact with the stream G1c.

According to a preferred embodiment, the process comprises a stage c), subsequent to stage b5) or to stage b7), in which the stream G1c″ obtained in stage b5) or the stream G1c″″ obtained in stage b7) comprises 2,3,3,3-tetrafluoropropene (HFO-1234yf), 1,1,1,2,2-pentafluoropropane (HFC-245cb) and trans-1,3,3,3-tetrafluoro-1-propene (HFO-1234zeE); and said stream G1c″ or G1c″″ is distilled in order to form a stream G1e′ comprising 2,3,3,3-tetrafluoropropene (HFO-1234yf) and 1,1,1,2,2-pentafluoropropane (HFC-245cb) and a stream G1h′ comprising trans-1,3,3,3-tetrafluoro-1-propene (HFO-1234zeE); advantageously, the stream G1c″ or G1c″″ is distilled by extractive distillation; preferably, the stream G1c″ or G1c″″ is distilled by extractive distillation by the stages:

c1′) bringing said stream G1c″ or G1c″″ into contact with an organic extraction agent in order to form a stream G1g′, and
c2′) extractive distillation of the stream G1g′ in order to form the flow G1e′ comprising 2,3,3,3-tetrafluoropropene (HFO-1234yf) and 1,1,1,2,2-pentafluoropropane (HFC-245cb), advantageously at the distillation column top, and the stream G1h′ comprising trans-1,3,3,3-tetrafluoro-1-propene (HFO-1234zeE) and said organic extraction agent, advantageously at the distillation column bottom.

According to a preferred embodiment, said liquid stream L1 comprises a part of the intermediate products B and all or part of the byproducts C, and a part of the liquid stream L1 is brought to low temperature, advantageously between −50° C. and 20° C., in order to form a first phase L1a comprising a part of the unreacted HF and a second phase L1b comprising said intermediate products B and said byproducts C; optionally or not, said stream G1d formed in stage b2) is mixed with the liquid stream L1 before the latter is brought to low temperature; advantageously, said first phase L1a is recycled in stage a);

advantageously, said second phase L1b is distilled in order to recover a stream L1c comprising 1,1,1,2,2-pentafluoropropane (HFC-245cb) and trans-1,3,3,3-tetrafluoro-1-propene (HFO-1234zeE), advantageously at the distillation column top, and a stream L1d comprising 2-chloro-3,3,3-trifluoro-1-propene (HCFO-1233xf), E-1-chloro-3,3,3-trifluoro-1-propene (HCFO-1233zdE) and 1,1,1,3,3-pentafluoropropane (HFC-245fa), advantageously at the distillation column bottom; advantageously, said stream L1c is recycled in stage a);

preferably, said stream L1d is separated by extractive distillation in order to form a flow comprising 2-chloro-3,3,3-trifluoro-1-propene (HCFO-1233xf) and a stream comprising E-1-chloro-3,3,3-trifluoro-1-propene (HCFO-1233zdE) and 1,1,1,3,3-pentafluoropropane (HFC-245fa).

DETAILED DESCRIPTION OF THE INVENTION

Figure 1:
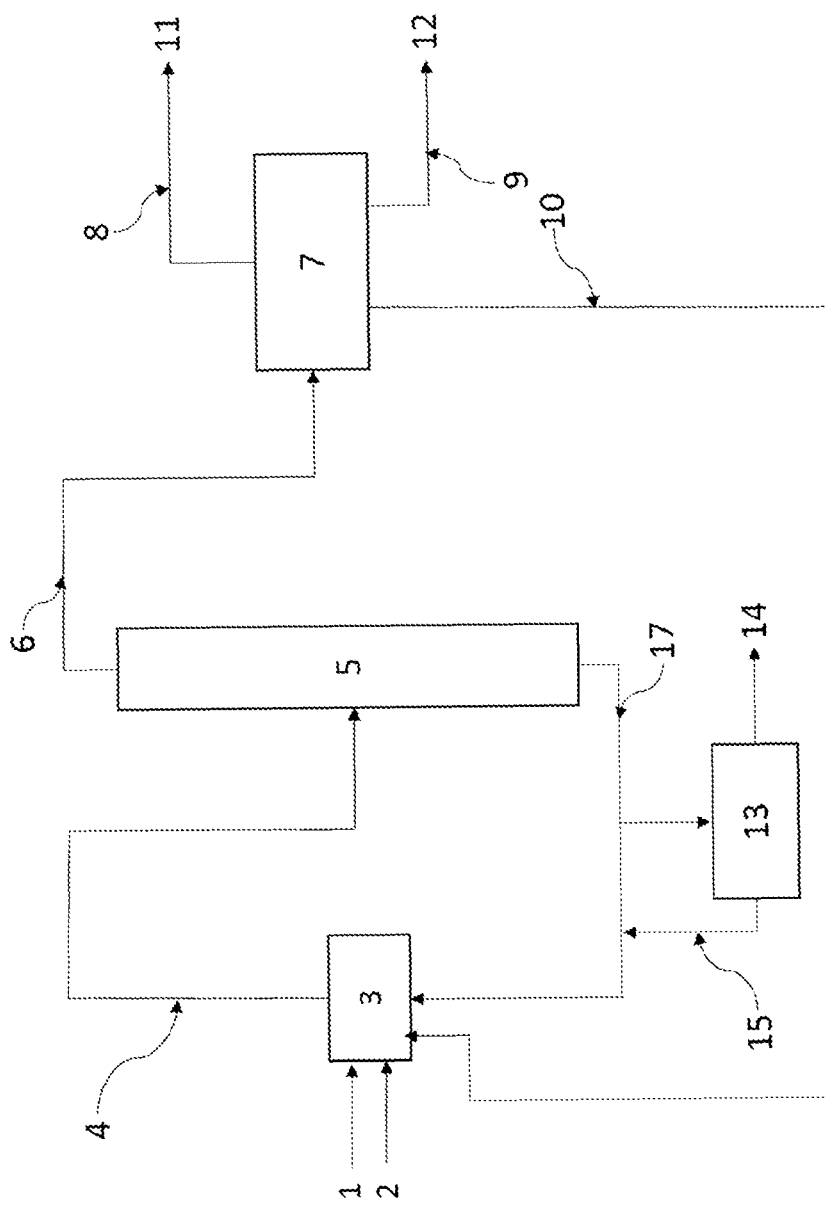
FIG. 1 diagrammatically represents a device which implements a process for the production of 2,3,3,3-tetrafluoro-1-propene according to a specific embodiment of the present invention.

The present invention makes possible the production and the purification of 2,3,3,3-tetrafluoropropene (HFO-1234yf). According to a first aspect of the present invention, a process for the production and purification of 2,3,3,3-tetrafluoropropene (HFO-1234yf) is provided. Said process is carried out starting from a starting composition comprising at least one compound of formula (I) $CH_{(n+2)}(X)_m$—$CH_p(X)_{(n+1)}$—$CX_{(3+p-m)}$, where X independently represents F or Cl; n, m and p are, independently of one another, 0 or 1 with n+m=0 or 1, n+p=0 or 1 and m−p=0 or 1, at least one X being Cl.

Preferably, said process comprises stage a) of bringing the starting composition into contact, in the presence of a catalyst, with HF under conditions effective in producing a composition A comprising HCl, a part of the unreacted HF, 2,3,3,3-tetrafluoropropene (HFO-1234yf), intermediate products B consisting of 2-chloro-3,3,3-trifluoropropene (HCFO-1233xf), 1,1,1,2,2-pentafluoropropane (HFC-245cb) and trans-1,3,3,3-tetrafluoro-1-propene (HFO-1234zeE) and byproducts C consisting of trans-1-chloro-3,3,3-trifluoro-1-propene (HCFO-1233zdE), cis-1-chloro-3,3,3-trifluoro-1-propene (HCFO-1233zdZ), cis-1,3,3,3-tetrafluoro-1-propene (HFO-1234zeZ), 1,1,1,3,3-pentafluoropropane (HFC-245fa), 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe), 1,1,1,3,3,3-hexafluoropropane (HFC-236fa) and optionally one or more compounds of formula (II) $C_nH_xF_yCl_z$ in which n=4, 5 or 6, x is an integer from 0 to 6, y is an integer from 4 to 12, z is an integer from 0 to 6, with 2n=x+y+z if w is 1 or 2n−2=x+y+z if w is 2 or 2n+2=x+y+z if w=0, w being the number of unsaturations in the compound of formula (II) considered.

Said byproducts C can also comprise one or more isomers of chloropentafluoropropane (HCFC-235), other than 2-chloro-1,1,1,3,3-pentafluoropropane (HCFC-235da). Said byproducts C can also comprise one or more isomers of dichlorotrifluoropropene (HCFO-1223), other than 1,2-dichloro-3,3,3-trifluoropropene (HCFO-1223xd). Said byproducts C can also comprise one or more isomers of chlorotetrafluoropropene (HCFO-1224), other than 2-chloro-1,3,3,3-tetrafluoropropene (HCFO-1224xe).

Preferably, said byproducts C can also comprise one or more compounds of formula (II) $C_nH_xF_yCl_z$, in which n=4, 5 or 6, x is an integer from 0 to 4, y is an integer from 6 to 12, z is an integer from 0 to 2, with 2n=x+y+z if w is 1 or 2n−2=x+y+z if w is 2 or 2n+2=x+y+z if w=0, w being the number of unsaturations in the compound of formula (II) considered.

In particular, the compounds of formula (II) are selected from the group consisting of hexafluorobutene (HFO-1336), chlorohexafluorobutene (HCFO-1326), heptafluorobutene (HFO-1327), octafluorobutane (HFC-338), dichlorooctafluoropentene (HCFO-1418), chlorononafluoropentene (HCFO-1419), chlorooctafluoropentene (HCFO-1428), nonafluoropentene (HFO-1429), octafluoropentene (HFO-1438), heptafluoropentene (HFO-1447), chlorononafluorohexene (HCFO-1539), chloroheptafluorohexene (HCFO-1557), decafluorohexene, undecafluorohexene and chlorooctafluorohexadiene (HCFO-2528). The compounds of formula (II) can exist under different isomeric forms which are encompassed in the present patent application.

Said composition produced in stage a) is recovered and purified. Preferably, the purification is carried out by distillation.

Preferably, the purification of said composition A carried out in stage b) comprises the distillation of said composition A in order to recover, at the distillation column top, a gas stream G1 comprising HCl, a part of the unreacted HF and 2,3,3,3-tetrafluoropropene (HFO-1234yf) and, at the distillation column bottom, a liquid stream L1 comprising a part of the unreacted HF. All or part of the intermediate products B and all or part of the byproducts C can be contained in said gas stream G1 and/or in said liquid stream L1.

Preferably, all or part of the 1,1,1,2,2-pentafluoropropane (HFC-245cb) can be contained in said gas stream G1. All or part of the 1,1,1,2,2-pentafluoropropane (HFC-245cb) can also be contained in said liquid stream L1.

Preferably, all or part of the trans-1,3,3,3-tetrafluoro-1-propene (HFO-1234zeE) can be contained in said gas stream G1. All or part of the trans-1,3,3,3-tetrafluoro-1-propene (HFO-1234zeE) can also be contained in said liquid stream L1.

Preferably, all or part of the 2-chloro-3,3,3-trifluoropropene (HCFO-1233xf) can be contained in said gas stream G1. All or part of the 2-chloro-3,3,3-trifluoropropene (HCFO-1233xf) can also be contained in said liquid stream L1. Favorably, a part of the 2-chloro-3,3,3-trifluoropropene (HCFO-1233xf) is contained in said liquid stream L1; advantageously, at least 70%, at least 75%, at least 80%, at least 85% or at least 90% of the 2-chloro-3,3,3-trifluoropropene (HCFO-1233xf) initially present in the composition A is contained in said liquid stream L1, the remainder occurring in said gas stream G1.

Preferably, all or part of the E-1-chloro-3,3,3-trifluoro-1-propene (HCFO-1233zdE) can be contained in said gas stream G1. All or part of the E-1-chloro-3,3,3-trifluoro-1-propene (HCFO-1233zdE) can also be contained in said liquid stream L1. Favorably, a part of the E-1-chloro-3,3,3-trifluoro-1-propene (HCFO-1233zdE) is contained in said liquid stream L1; advantageously, at least 70%, at least 75%, at least 80%, at least 85% or at least 90% of the 1-chloro-3,3,3-trifluoro-1-propene (HCFO-1233zd) initially present in the composition A is contained in said liquid stream L1, the remainder occurring in said gas stream G1.

Preferably, all or part of the 1,1,1,3,3-pentafluoropropane (HFC-245fa) can be contained in said gas stream G1. All or part of the 1,1,1,3,3-pentafluoropropane (HFC-245fa) can also be contained in said liquid stream L1. Favorably, a part of the 1,1,1,3,3-pentafluoropropane (HFC-245fa) is contained in said liquid stream L1; advantageously, at least 70%, at least 75%, at least 80%, at least 85% or at least 90% of the 1,1,1,3,3-pentafluoropropane (HFC-245fa) initially present in the composition A is contained in said liquid stream L1, the remainder occurring in said gas stream G1.

Preferably, said liquid stream L1 comprises at least 70 mol % of hydrofluoric acid, advantageously at least 75 mol % of hydrofluoric acid, preferably at least 80 mol % of hydrofluoric acid, more preferably at least 85 mol % of hydrofluoric acid, in particular at least 90 mol % of hydrofluoric acid.

In particular, the recovery of said composition A and its purification, preferably by distillation, makes it possible to form and to recover a gas stream G1 comprising HCl, 2,3,3,3-tetrafluoropropene (HFO-1234yf), a part of the unreacted HF, a part of the intermediate products B and a part of the byproducts C, preferably at the distillation column top, and a liquid stream L1 comprising a part of the unreacted HF, a part of the intermediate products B and a part of the byproducts C, preferably at the distillation column bottom.

Stage b) of the present process can be carried out by distillation at a pressure of 2 to 8 bara, advantageously of 3 to 6 bara, preferably of 3.5 to 5.5 bara, in particular at a pressure of 4 bara. Stage b) of the present process can be carried out by distillation so as to obtain a distillation column top temperature of −30° C. to 20° C., advantageously of −20° C. to 10° C., preferably of −15° C. to 0° C. Stage b) of the present process can be carried out by distillation so as to obtain a distillation column bottom temperature of 10° C. to 100° C., advantageously of 20° C. to 90° C., preferably of 30° C. to 80° C., in particular of 40° C. to 70° C.

According to a preferred embodiment, said first stream is a gas stream G1 purified by the following stages:

b1) distillation of the gas stream G1 in order to recover a stream G1a comprising HCl, advantageously at the distillation column top, and a stream G1b comprising 2,3,3,3-tetrafluoropropene (HFO-1234yf), a part of the unreacted HF, said a part of the intermediate products B and said a part of the byproducts C, advantageously at the distillation column bottom;

b2-1) distillation of said stream G1b obtained in stage b1) under conditions effective in forming a gas stream G1c comprising 2,3,3,3-tetrafluoropropene (HFO-1234yf), a portion of said part of said unreacted HF, a portion of said part of the intermediate products B, advantageously at the distillation column top, and a liquid stream G1d comprising a portion of said part of the intermediate products B and said part of the byproducts C and a portion of said part of said unreacted HF, advantageously at the distillation column bottom;

b2-2) distillation of said stream G1d obtained in stage b2-1) under conditions effective in forming a stream G1d' comprising said portion of said part of the intermediate products B, said portion of said part of said unreacted HF and a portion of said part of the byproducts C comprising cis-1,3,3,3-tetrafluoro-1-propene (HFO-1234zeZ), 1,1,1,3,3,3-hexafluoropropane (HFC-236fa) and a part of trans-1-chloro-3,3,3-trifluoro-1-propene (HCFO-1233zdE) and 1,1,1,3,3-pentafluoropropane (HFC-245fa); and a stream G1d" comprising a portion of said part of the byproducts C comprising cis-1-chloro-3,3,3-trifluoro-1-propene (HCFO-1233zdZ), 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe), and optionally one or more compounds of formula (II) $C_nH_xF_yCl_z$ in which n=4, 5 or 6, x is an integer from 0 to 6, y is an integer from 4 to 12, z is an integer from 0 to 6, with 2n=x+y+z if w is 1 or 2n−2=x+y+z if w is 2 or 2n+2=x+y+z if w=0, w being the number of unsaturations in the compound of formula (II) considered.

According to a preferred embodiment, the distillation column top temperature in stage b1) can be from −10° C. to −70° C., preferably from −15° C. to −65° C., in particular from −20° C. to −60° C., more particularly from −25° C. to −60° C., favorably from −30° C. to −60° C. Preferably, the distillation column top pressure in stage b1) is from 2 to 20 bara, advantageously from 3 to 15 bara, preferably from 4 to 10 bara.

According to a preferred embodiment, the distillation column top temperature in stage b2-1) is between 0° C. and 50° C. Preferably, the distillation column top pressure in stage b2-1) is between 3 and 12 bara.

Preferably, the content of 2,3,3,3-tetrafluoropropene in the stream G1c is greater than 40% by weight, advantageously greater than 45% by weight, preferably greater than 50% by weight, more preferably greater than 55% by weight, in particular greater than 60% by weight, more particularly greater than 65% by weight, favorably greater than 70% by weight, based on the total weight of the stream G1c.

Preferably, the content of intermediate products B in said stream G1c is between 5% and 40% by weight, based on the total weight of said stream G1c, advantageously between 10% and 35% by weight, based on the total weight of said stream G1c, preferably between 15% and 30% by weight, based on the total weight of said stream G1c.

Preferably, the content of trans-1,3,3,3-tetrafluoropropene in said stream G1c is less than 15% by weight, based on the total weight of said stream G1c, advantageously less than 12% by weight, preferably less than 10% by weight, more preferably less than 8% by weight, in particular less than 6% by weight, more particularly less than 5% by weight, based on the total weight of said stream G1c.

Preferably, the content of 2-chloro-3,3,3-trifluoropropene in said stream G1c is less than 0.5% by weight, based on the total weight of said stream G1c, advantageously less than 0.1% by weight, preferably less than 500 ppm by weight, more preferably less than 250 ppm by weight, in particular less than 100 ppm by weight, more particularly less than 50 ppm by weight, based on the total weight of said stream G1c.

Preferably, the content of 1,1,1,2,2-pentafluoropropane in said stream G1c is less than 40% by weight, based on the total weight of said stream G1c, advantageously less than 35% by weight, preferably less than 30% by weight, more preferably less than 25% by weight, in particular less than 22% by weight, more particularly less than 20% by weight, based on the total weight of said stream G1c.

Preferably, the content of hydrofluoric acid in said stream G1c is less than 20% by weight, based on the total weight of said stream G1c, advantageously less than 18% by weight, preferably less than 16% by weight, more preferably less than 14% by weight, in particular less than 12% by weight, more particularly less than 10% by weight, based on the total weight of said stream G1c.

Preferably, the content of intermediate products B in said stream G1d is between 60% and 90% by weight, based on the total weight of said stream G1d, advantageously between 70% and 90% by weight, based on the total weight of said stream G1d, preferably between 75% and 85% by weight, based on the total weight of said stream G1d.

Preferably, the content of trans-1,3,3,3-tetrafluoropropene in said stream G1d is less than 10% by weight, based on the total weight of said stream G1d, advantageously less than 9% by weight, preferably less than 8% by weight, more preferably less than 7% by weight, in particular less than 6% by weight, more particularly less than 5% by weight, based on the total weight of said stream G1d.

Preferably, the content of 2-chloro-3,3,3-trifluoropropene in said stream G1d is less than 25% by weight, based on the total weight of said stream G1d, advantageously less than 24% by weight, preferably less than 23% by weight, more preferably less than 22% by weight, in particular less than 21% by weight, more particularly less than 20% by weight, based on the total weight of said stream G1d.

Preferably, the content of 1,1,1,2,2-pentafluoropropane in said stream G1d is less than 75% by weight, based on the total weight of said stream G1d, advantageously less than 74% by weight, preferably less than 73% by weight, more preferably less than 72% by weight, in particular less than 71% by weight, more particularly less than 70% by weight, based on the total weight of said stream G1d.

Preferably, the content of hydrofluoric acid in said stream G1d is less than 15% by weight, based on the total weight of said stream G1d, advantageously less than 14% by weight, preferably less than 13% by weight, more preferably less than 12% by weight, based on the total weight of said stream G1d.

According to a preferred embodiment, the distillation column top temperature used in stage b2-2) is from 0° C. to 60° C., preferably from 10° C. to 45° C. In particular, the distillation column top pressure used in stage b2-2) is from 1 to 10 bara, preferably from 2 to 8 bara.

Preferably, the stream G1d' is in liquid form. Preferably, the stream G1d" is in liquid form.

Preferably, at least 90% of the 1,1,1,2,2-pentafluoropropane contained in the stream G1d is recovered in the stream G1d'; advantageously, at least 91%, preferably at least 92%, more preferably at least 93%, in particular at least 94%, more particularly at least 95%, favorably at least 96%, preferentially favorably at least 97%, particularly favorably at least 98%, of the 1,1,1,2,2-pentafluoropropane and of the trans-1,3,3,3-tetrafluoropropene contained in the stream G1d are recovered in the stream G1d'.

Preferably, at least 90% of the trans-1,3,3,3-tetrafluoropropene contained in the stream G1d is recovered in the stream G1d'; advantageously, at least 91%, preferably at least 92%, more preferably at least 93%, in particular at least 94%, more particularly at least 95%, favorably at least 96%, preferentially favorably at least 97%, particularly favorably at least 98%, of the trans-1,3,3,3-tetrafluoropropene contained in the stream G1d is recovered in the stream G1d'.

Preferably, at least 90% of the 1,1,1,2,2-pentafluoropropane and of the trans-1,3,3,3-tetrafluoropropene contained in the stream G1d are recovered in the stream G1d'; advantageously, at least 91%, preferably at least 92%, more preferably at least 93%, in particular at least 94%, more particularly at least 95%, favorably at least 96%, preferentially favorably at least 97%, particularly favorably at least 98%, of the 1,1,1,2,2-pentafluoropropane and of the trans-1,3,3,3-tetrafluoropropene contained in the stream G1d are recovered in the stream G1d'.

Preferably, at least 50% of the 2-chloro-3,3,3-trifluoropropene contained in the stream G1d is recovered in the stream G1d'; advantageously, at least 55%, preferably at least 60%, more preferably at least 65%, in particular at least 70%, more particularly at least 75%, of the 2-chloro-3,3,3-trifluoropropene contained in the stream G1d is recovered in the stream G1d'.

Preferably, the stream G1d' comprises from 60% to 70% by weight of 1,1,1,2,2-pentafluoropropane, from 1% to 5% by weight of trans-1,3,3,3-tetrafluoropropene and from 10% to 15% by weight of 2-chloro-3,3,3-trifluoropropene, based on the total weight of the stream G1d'.

Preferably, at least 85% of the cis-1,3,3,3-tetrafluoro-1-propene (HFO-1234zeZ) contained in the stream G1d is recovered in the stream G1d'; advantageously, at least 90%, preferably at least 92%, more preferably at least 93%, in particular at least 95%, more particularly at least 97%, of the cis-1,3,3,3-tetrafluoro-1-propene (HFO-1234zeZ) contained in the stream G1d is recovered in the stream G1d'.

Preferably, at least 85% of the 1,1,1,3,3,3-hexafluoropropane (HFC-236fa) contained in the stream G1d is recovered in the stream G1d'; advantageously, at least 90%, preferably at least 92%, more preferably at least 93%, in particular at least 95%, more particularly at least 97%, of the 1,1,1,3,3,3-hexafluoropropane (HFC-236fa) contained in the stream G1d is recovered in the stream G1d'.

Preferably, at least 85% of the cis-1,3,3,3-tetrafluoro-1-propene (HFO-1234zeZ) and of the 1,1,1,3,3,3-hexafluoropropane (HFC-236fa) contained in the stream G1d are recovered in the stream G1d'; advantageously, at least 90%, preferably at least 92%, more preferably at least 93%, in particular at least 95%, more particularly at least 97% advantageously at least 90%, preferably at least 92%, more preferably at least 93%, in particular at least 95%, more particularly at least 97%, of the cis-1,3,3,3-tetrafluoro-1- propene (HFO-1234zeZ) and of the 1,1,1,3,3,3-hexafluoropropane (HFC-236fa) contained in the stream G1d are recovered in the stream G1d'.

Preferably, the stream G1d' comprises from 60% to 70% by weight of 1,1,1,2,2-pentafluoropropane, from 1% to 5% by weight of trans-1,3,3,3-tetrafluoropropene, from 10% to 15% by weight of 2-chloro-3,3,3-trifluoropropene, from 0.1% to 0.5% by weight of cis-1,3,3,3-tetrafluoro-1-propene (HFO-1234zeZ) and from 1% to 5% by weight of 1,1,1,3,3,3-hexafluoropropane (HFC-236fa), based on the total weight of the stream G1d'.

Preferably, at least 40% of the trans-1-chloro-3,3,3-trifluoropropene (HCFO-1233zdE) contained in the stream G1d is recovered in the stream G1d'; advantageously, at least 50%, preferably at least 55%, more preferably at least 60%, in particular at least 65%, more particularly at least 70%, of the trans-1-chloro-3,3,3-trifluoropropene (HCFO-1233zdE) contained in the stream G1d is recovered in the stream G1d'.

Preferably, at least 40% of the 1,1,1,3,3-pentafluoropropane (HFC-245fa) contained in the stream G1d is recovered in the stream G1d'; advantageously, at least 50%, preferably at least 55%, more preferably at least 60%, in particular at least 65%, more particularly at least 70%, of the 1,1,1,3,3-pentafluoropropane (HFC-245fa) contained in the stream G1d is recovered in the stream G1d'.

Preferably, the stream G1d' comprises from 0.1% to 0.5% by weight of cis-1,3,3,3-tetrafluoro-1-propene (HFO-1234zeZ), from 1.0% to 5.0% by weight of 1,1,1,3,3,3-hexafluoropropane (HFC-236fa), from 0.5% to 2.0% by weight of trans-1-chloro-3,3,3-trifluoro-1-propene (HCFO-1233zdE) and from 0.1% to 1.0% by weight of 1,1,1,3,3-pentafluoropropane (HFC-245fa), based on the total weight of the stream G1d'.

Preferably, the stream G1d' comprises from 60% to 70% by weight of 1,1,1,2,2-pentafluoropropane, from 1.0% to 5.0% by weight of trans-1,3,3,3-tetrafluoropropene, from 10% to 15% by weight of 2-chloro-3,3,3-trifluoropropene, from 0.1% to 0.5% by weight of cis-1,3,3,3-tetrafluoro-1-propene (HFO-1234zeZ), from 1.0% to 5.0% by weight of 1,1,1,3,3,3-hexafluoropropane (HFC-236fa), from 0.1% to 1.0% by weight of 1,1,1,3,3-pentafluoropropane (HFC-245fa) and from 0.5% to 2.0% by weight of trans-1-chloro-3,3,3-trifluoropropene (HCFO-1233zdE), based on the total weight of the stream G1d'.

Preferably, the stream G1d' comprises from 10% to 20% by weight of hydrofluoric acid, based on the total weight of the stream G1d'.

Preferably, the stream G1d' also comprises 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe) in a low content. In particular, the content of 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe) in the stream G1d' is less than 5% by weight, based on the total weight of G1d', advantageously less than 4% by weight, preferably less than 3% by weight, more preferably less than 2% by weight, in particular less than 1% by weight, more particularly less than 0.5% by weight, based on the total weight of G1d'.

Preferably, said stream G1d' is devoid of the other byproducts C as described above. The other byproducts C are cis-1-chloro-3,3,3-trifluoro-1-propene (HCFO-1233zdZ) and one or more compounds of formula (II). Alternatively, said stream G1d' can comprise a very low content of the other byproducts C as described above. Preferably, if the stream G1d' contains them, the content of each of the other byproducts C is less than 1% by weight, based on the total weight of said stream G1d', advantageously less than 0.5% by weight, preferably less than 0.1% by weight, more preferably less than 0.05% by weight, in particular less than 0.01% by weight, more particularly less than 0.005% by weight, based on the total weight of said stream G1d'. In particular, if the stream G1d' contains them, the total content of cis-1-chloro-3,3,3-trifluoro-1-propene (HCFO-1233zdZ) and one or more compounds of formula (II) is less than 1% by weight, based on the total weight of said stream G1d', advantageously less than 0.5% by weight, preferably less than 0.1% by weight, more preferably less than 0.05% by weight, in particular less than 0.01% by weight, more particularly less than 0.005% by weight, based on the total weight of said stream G1d'.

Preferably, the stream G1d' is recycled in stage a).

Preferably, at least 95% of the cis-1-chloro-3,3,3-trifluoro-1-propene (HCFO-1233zdZ) contained in the stream G1d is recovered in the stream G1d"; advantageously, at least 96%, preferably at least 97%, more preferably at least 98%, in particular at least 99%, more particularly at least 99.5%, of the cis-1-chloro-3,3,3-trifluoro-1-propene (HCFO-1233zdZ) contained in the stream G1d is recovered in the stream G1d".

Preferably, at least 95% of said one or more compounds of formula (II) contained in the stream G1d is recovered in the stream G1d"; advantageously, at least 96%, preferably at least 97%, more preferably at least 98%, in particular at least 99%, more particularly at least 99.5%, of said one or more compounds of formula (II) contained in the stream G1d is recovered in the stream G1d".

Preferably, at least 80% of the 2-chloro-1,1,1,3,3-pentafluoropropane (HCFC-235da) contained in the stream G1d is recovered in the stream G1d"; advantageously, at least 85%, preferably at least 90%, more preferably at least 93%, in particular at least 94%, more particularly at least 95%, of the 2-chloro-1,1,1,3,3-pentafluoropropane (HCFC-235da) contained in the stream G1d is recovered in the stream G1d". In particular, from 90% to 98% of the 2-chloro-1,1,1,3,3-pentafluoropropane (HCFC-235da) contained in the stream G1d is recovered in the stream G1d".

Preferably, at least 80% of the 1,2-dichloro-3,3,3-trifluoropropene (HCFO-1223xd) contained in the stream G1d is recovered in the stream G1d"; advantageously, at least 85%, preferably at least 90%, more preferably at least 93%, in particular at least 94%, more particularly at least 95%, of the 1,2-dichloro-3,3,3-trifluoropropene (HCFO-1223xd) contained in the stream G1d is recovered in the stream G1d". In particular, from 90% to 98% of the 1,2-dichloro-3,3,3-trifluoropropene (HCFO-1223xd) contained in the stream G1d is recovered in the stream G1d".

Preferably, at least 80% of the 2-chloro-1,3,3,3-tetrafluoropropene (HCFO-1224xe) contained in the stream G1d is recovered in the stream G1d"; advantageously, at least 85%, preferably at least 90%, more preferably at least 93%, in particular at least 94%, more particularly at least 95%, of the 2-chloro-1,3,3,3-tetrafluoropropene (HCFO-1224xe) contained in the stream G1d is recovered in the stream G1d". In particular, from 90% to 98% of the 2-chloro-1,3,3,3-tetrafluoropropene (HCFO-1224xe) contained in the stream G1d is recovered in the stream G1d".

Preferably, said stream G1d" comprises from 1% to 25% by weight of 2-chloro-1,3,3,3-tetrafluoropropene (HCFO-1224xe), advantageously from 5% to 20% by weight, preferably from 7% to 18% by weight, in particular from 10% to 15% by weight, of 2-chloro-1,3,3,3-tetrafluoropropene (HCFO-1224xe), based on the total weight of said stream G1d".

Preferably, said stream G1d" comprises from 40% to 85% by weight of 1,2-dichloro-3,3,3-trifluoropropene (HCFO-1223xd), advantageously from 45% to 80% by weight, preferably from 50% to 75% by weight, in particular from 55% to 70% by weight, of 1,2-dichloro-3,3,3-trifluoropropene (HCFO-1223xd), based on the total weight of said stream G1d".

Preferably, said stream G1d" comprises from 1% to 25% by weight of 2-chloro-1,1,1,3,3-pentafluoropropane (HCFC-235da), advantageously from 5% to 20% by weight, preferably from 7% to 18% by weight, in particular from 10% to 15% by weight, of 2-chloro-1,1,1,3,3-pentafluoropropane (HCFC-235da), based on the total weight of said stream G1d".

Preferably, said stream G1d" comprises from 0.05% to 10% by weight of cis-1-chloro-3,3,3-trifluoro-1-propene (HCFO-1233zdZ), advantageously from 0.1% to 8% by weight, preferably from 0.5% to 7% by weight, in particular from 1% to 5% by weight, of cis-1-chloro-3,3,3-trifluoro-1-propene (HCFO-1233zdZ), based on the total weight of said stream G1d".

Preferably, said stream G1d" comprises from 0.1% to 10% by weight of one or more compounds of formula (II), advantageously from 0.25% to 7.5% by weight, preferably from 0.5% to 5% by weight, in particular from 1% to 5% by weight, of one or more compounds of formula (II), based on the total weight of said stream G1d".

Thus, said stream G1d" can comprise from 1% to 5% by weight of cis-1-chloro-3,3,3-trifluoro-1-propene (HCFO-1233zdZ), from 10% to 15% by weight of 2-chloro-1,1,1,3,3-pentafluoropropane (HCFC-235da), from 55% to 70% by weight of 1,2-dichloro-3,3,3-trifluoropropene (HCFO-1223xd), from 10% to 15% by weight of 2-chloro-1,3,3,3-tetrafluoropropene (HCFO-1224xe) and from 1% to 5% by weight of said one or more compounds of formula (II), based on the total weight of the stream G1d".

Preferably, at most 15% of the cis-1,3,3,3-tetrafluoro-1-propene (HFO-1234zeZ) contained in the stream G1d is recovered in the stream G1d'; advantageously, at most 10%, preferably at most 8%, more preferably at most 7%, in particular at most 5%, more particularly at most 3%, of the cis-1,3,3,3-tetrafluoro-1-propene (HFO-1234zeZ) contained in the stream G1d is recovered in the stream G1d".

Preferably, at most 15% of the 1,1,1,3,3,3-hexafluoropropane (HFC-236fa) contained in the stream G1d is recovered in the stream G1d"; advantageously, at most 10%, preferably at most 8%, more preferably at most 7%, in particular at most 5%, more particularly at most 3%, of the 1,1,1,3,3,3-hexafluoropropane (HFC-236fa) contained in the stream G1d is recovered in the stream G1d".

Preferably, at most 15% of the cis-1,3,3,3-tetrafluoro-1-propene (HFO-1234zeZ) and of the 1,1,1,3,3,3-hexafluoropropane (HFC-236fa) contained in the stream G1d are recovered in the stream G1d'; advantageously, at most 10%, preferably at most 8%, more preferably at most 7%, in particular at most 5%, more particularly at most 3%, of the cis-1,3,3,3-tetrafluoro-1-propene (HFO-1234zeZ) and of the 1,1,1,3,3,3-hexafluoropropane (HFC-236fa) contained in the stream G1d are recovered in the stream G1d".

Preferably, at most 60% of the trans-1-chloro-3,3,3-trifluoropropene (HCFO-1233zdE) contained in the stream G1d is recovered in the stream G1d"; advantageously, at most 50%, preferably at most 45%, more preferably at most 40%, in particular at most 35%, more particularly at most 30%, of the trans-1-chloro-3,3,3-trifluoropropene (HCFO-1233zdE) contained in the stream G1d is recovered in the stream G1d".

Preferably, at most 60% of the 1,1,1,3,3-pentafluoropropane (HFC-245fa) contained in the stream G1d is recovered in the stream G1d"; advantageously, at most 50%, preferably at most 45%, more preferably at most 40%, in particular at most 35%, more particularly at most 30%, of the 1,1,1,3,3-pentafluoropropane (HFC-245fa) contained in the stream G1d is recovered in the stream G1d".

Preferably, the stream G1d" comprises from 0.01% to 0.05% by weight of cis-1,3,3,3-tetrafluoro-1-propene (HFO-1234zeZ), from 0.05% to 0.5% by weight of 1,1,1,3,3,3-hexafluoropropane (HFC-236fa), from 0.05% to 0.5% by weight of trans-1-chloro-3,3,3-trifluoro-1-propene (HCFO-1233zdE) and from 0.05% to 0.5% by weight of 1,1,1,3,3-pentafluoropropane (HFC-245fa), based on the total weight of the stream G1d".

Preferably, the stream G1d" comprises less than 2% by weight of hydrofluoric acid, based on the total weight of the stream G1d", advantageously less than 1% by weight, preferably less than 0.5% by weight, in particular less than 0.1% by weight, of hydrofluoric acid, based on the total weight of the stream G1d".

Preferably, at most 50% of the 2-chloro-3,3,3-trifluoropropene contained in the stream G1d is recovered in the stream G1d"; advantageously, at most 45%, preferably at most 40%, more preferably at most 35%, in particular at most 30%, more particularly at most 25%, of the 2-chloro-3,3,3-trifluoropropene contained in the stream G1d is recovered in the stream G1d".

Preferably, the stream G1d" comprises from 1% to 25% by weight of 2-chloro-3,3,3-trifluoropropene, based on the total weight of the stream G1d", advantageously from 5% to 20% by weight, preferably from 7% to 18% by weight, in particular from 10% to 15% by weight, of 2-chloro-3,3,3-trifluoropropene, based on the total weight of the stream G1d".

Preferably, the process also comprises the stages:

b3) bringing the stream G1c obtained in stage b2-1) into contact with an aqueous hydrofluoric acid solution with a concentration of greater than 40% in order to form a two-phase stream G1c' comprising 2,3,3,3-tetrafluoropropene (HFO-1234yf), hydrofluoric acid, a portion of said part of the intermediate products B and a portion of said part of the byproducts C, b4) storage of said stream G1c' in a holding tank, said stream G1c' being a two-phase stream consisting of a liquid phase and of a gas phase, b5) passage of the gas phase of said stream G1c' into an absorption column fed countercurrentwise with an aqueous flow in order to form a stream G1c" comprising 2,3,3,3-tetrafluoropropene (HFO-1234yf), a portion of said part of the intermediate products B and a portion of said part of the byproducts C and a stream G1c'" comprising HF.

Preferably, the stream G1c formed in stage b2-1) can comprise 2,3,3,3-tetrafluoropropene (HFO-1234yf), 1,1,1,2,2-pentafluoropropane (HFC-245cb) and 1,3,3,3-tetrafluoro-1-propene (HFO-1234ze).

Preferably, the aqueous hydrofluoric acid solution used in stage b3) has a concentration of greater than 40% by weight. In particular, the aqueous hydrofluoric acid solution has a concentration of greater than 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% by weight. More particularly, the aqueous hydrofluoric acid solution has a concentration of greater than or equal to 50% by weight or of greater than or equal to 60% by weight or of greater than or equal to 70% by weight.

More particularly, the aqueous hydrofluoric acid solution used in stage b3) can be between any one of the values mentioned above. Thus, the aqueous hydrofluoric acid solution can be between 45% and 95% by weight, between 50% and 90% by weight, between 55% and 85% by weight, between 60% and 80% by weight or between 65% and 75% by weight.

According to a preferred embodiment, the process also comprises the stages:

b6) neutralization of said stream G1c" obtained in stage b5) with an aqueous alkaline solution in order to form a neutralized stream, and b7) drying of said neutralized stream obtained in stage b6) over a molecular sieve, in order to form a neutralized and dried stream G1c"".

Preferably, the aqueous hydrofluoric acid solution used in stage b3) is at a temperature of between −20° C. and 80° C. before it is brought into contact with the stream G1c, advantageously between −15° C. and 70° C., preferably between −10° C. and 60° C., more preferably between −5° C. and 50° C., in particular between −5° C. and 40° C., more particularly between 0° C. and 30° C. Thus, in a particularly preferred embodiment, the temperature of the aqueous hydrofluoric acid solution used in stage b3), before it is brought into contact with the stream G1c, can be 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C. or 30° C. Said aqueous hydrofluoric acid solution is employed at the abovementioned temperatures in order to control the exothermicity occurring during the operation in which it is brought into contact with the stream G1c.

According to a preferred embodiment, said two-phase stream G1c' consists of a gas phase comprising 2,3,3,3-tetrafluoropropene (HFO-1234yf), a portion of said part of the intermediate products B and a portion of said part of the byproducts C. The gas phase may possibly comprise traces of hydrofluoric acid. In this case, the content of hydrofluoric acid in said gas phase of said two-phase stream is less than 5% by weight, based on the total weight of said gas phase, in particular less than 2% by weight, based on the total weight of said gas phase, more particularly less than 1% by weight, based on the total weight of said gas phase. The liquid phase of said two-phase stream comprises hydrofluoric acid. The liquid phase of said two-phase stream G1c' can also comprise less than 5% by weight, based on the total weight of said liquid phase, of organic compounds selected from the group consisting of 2,3,3,3-tetrafluoropropene (HFO-1234yf), a portion of said part of the intermediate products B and a portion of said part of the byproducts C; preferably less than 1% by weight, in particular less than 5000 ppm, more particularly less than 1000 ppm, favorably less than 500 ppm, particularly favorably less than 100 ppm, of organic compounds selected from the group consisting of 2,3,3,3-tetrafluoropropene (HFO-1234yf), a portion of said part of the intermediate products B and a portion of said part of the byproducts C, based on the total weight of said liquid phase.

Preferably, the concentration of hydrofluoric acid in said liquid phase of said two-phase stream G1c' is greater than the concentration of said aqueous hydrofluoric acid solution used in stage b3). Said liquid phase of said two-phase stream G1c' can have a concentration of hydrofluoric acid of greater than 41% by weight, based on the total weight of said liquid phase of said two-phase stream G1c'. Advantageously, said liquid phase of said two-phase stream G1c' can have a concentration of hydrofluoric acid of greater than 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% by weight, based on the total weight of said liquid phase of said two-phase stream G1c'. Preferably, said liquid phase of said two-phase stream G1c' can have a concentration of hydrofluoric acid of between 45% and 95% by weight, between 50% and 90% by weight, between 55% and 85% by weight, between 60% and 80% by weight or between 65% and 75% by weight, while being greater than the concentration of said aqueous hydrofluoric acid solution used in stage b3).

As mentioned above, stage b4) of the process according to the present invention employs the storing of said two-phase stream G1c' in a holding tank, said two-phase stream G1c' consisting of said liquid phase and of said gas phase as described above.

As mentioned above, stage b5) of the process according to the present invention employs passing the gas phase of said two-phase stream G1c' into an absorption column fed countercurrentwise with an aqueous flow, in order to form a stream G1c" comprising 2,3,3,3-tetrafluoropropene (HFO-1234yf), a portion of said part of the intermediate products B and a portion of said part of the byproducts C and a stream G1c'" comprising hydrofluoric acid.

Preferably, the flow rate of the aqueous flow used in stage b5) is determined as a function of the amount of hydrofluoric acid contained in said stream G1c. Thus, the ratio of the flow rate of the aqueous flow, expressed in kg/h, feeding the absorption column in stage b5) to the amount of hydrofluoric acid in said stream G1c, expressed in kg/h, is between 0.05 and 1.22. Advantageously, the ratio of the flow rate of the aqueous flow, expressed in kg/h, feeding the absorption column in stage b5) to the amount of hydrofluoric acid in said stream G1c, expressed in kg/h, can be from 0.11 to 1.00, preferably from 0.18 to 0.82, more preferably from 0.25 to 0.67, in particular from 0.33 to 0.54. Thus, the ratio of the flow rate of the aqueous flow, expressed in kg/h, feeding the absorption column in stage b5) to the amount of hydrofluoric acid in said stream G1c, expressed in kg/h, can be 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69 or 0.70. An additional aqueous stream corresponding to the fraction of water evaporated at the top of said absorption column can also feed said column. The aqueous flow described above is different from said additional aqueous stream related to the water fraction evaporated at the top of the column and does not encompass it.

According to a preferred embodiment, said absorption column employed in stage b5) comprises at least one absorption stage, advantageously two absorption stages. Preferably, said absorption column employed in stage b5) comprises at least three absorption stages. Said absorption column employed in stage b5) can thus comprise two, three, four, five, six, seven, eight, nine, ten, eleven, twelve, thirteen, fourteen or fifteen absorption stages.

The use of an absorption column having at least one stage, advantageously at least two absorption stages, preferably at least three absorption stages, makes it possible to obtain a stream G1c" having a low content of hydrofluoric acid. Advantageously, said stream G1c" comprises less than 1000 ppm of hydrofluoric acid by weight, based on the total weight of said stream G1c", preferably less than 900 ppm of hydrofluoric acid, more preferably less than 800 ppm of hydrofluoric acid, in particular less than 700 ppm of hydrofluoric acid, more particularly less than 600 ppm of hydrofluoric acid, favorably less than 500 ppm of hydrofluoric acid, more favorably still less than 400 ppm of hydrofluoric acid, preferably favorably less than 300 ppm of hydrofluoric acid, particularly favorably less than 200 ppm of hydrofluoric acid, more particularly favorably less than 100 ppm of hydrofluoric acid. Thus, said stream G1c" can have a content of hydrofluoric acid of between 1 and 200 ppm, between 5 and 190 ppm, between 10 and 180 ppm, between 15 and 170 ppm, between 20 and 160 ppm, between 25 and 150 ppm or between 30 and 140 ppm by weight, based on the total weight of said stream G1c". Said stream G1c" can have a content of hydrofluoric acid of less than 100 ppm, advantageously less than 75 ppm, preferably less than 50 ppm, more preferentially less than 30 ppm, in particular less than 15 ppm, more particularly less than 10 ppm by weight, based on the total weight of said stream G1c".

Preferably, at least 80% by weight of the hydrofluoric acid possibly present in said gas phase of said two-phase stream G1c' is absorbed by the first absorption stage of said absorption column, in particular at least 85% by weight of the hydrofluoric acid possibly present in said gas phase of said two-phase stream G1c' is absorbed by the first absorption stage of said absorption column, more particularly at least 90% by weight of the hydrofluoric acid possibly present in said gas phase of said two-phase stream G1c' is absorbed by the first absorption stage of said absorption column.

Preferably, said aqueous flow can be introduced at least at the level of the top of the absorption column. Preferably, the top temperature of said absorption column is from 20° C. to 70° C., preferably from 30° C. to 50° C.

According to a preferred embodiment, said stream G1c''' is in the form of an aqueous hydrofluoric acid solution. Advantageously, said stream G1c''' is a hydrofluoric acid solution with a concentration of less than 30% by weight, based on the total weight of said stream G1c'''. Preferably, said stream G1c''' is a hydrofluoric acid solution with a concentration of less than 25% by weight, based on the total weight of said stream G1c'''. In particular, said stream G1c''' is a hydrofluoric acid solution with a concentration of between 5% and 25% by weight, based on the total weight of said stream G1c''', more particularly between 10% and 20% by weight, based on the total weight of said stream G1c'''. According to a preferred embodiment, said stream G1c''' is recycled in stage b4). The stream G1c''' is thus mixed with the liquid phase of said stream G1c'.

According to a preferred embodiment, said process also comprises the stages of:

b6) neutralization of said stream G1c" obtained in stage b5) with an aqueous alkaline solution in order to form a neutralized stream, and b7) drying of said neutralized stream obtained in stage b6), preferably over a molecular sieve, in order to form a neutralized and dried stream G1c''''.

According to a preferred embodiment, said aqueous alkaline solution can be an aqueous solution of hydroxide of an alkali metal or alkaline earth metal. The aqueous alkaline solution can be an aqueous solution of sodium hydroxide, of potassium hydroxide, of calcium hydroxide or of magnesium hydroxide or a mixture of these. Preferably, said aqueous alkaline solution exhibits a concentration of between 5% and 50% by weight, based on the total weight of said aqueous alkaline solution. Advantageously, said aqueous alkaline solution exhibits a concentration of at least 5%, of at least 6%, of at least 7%, of at least 8%, of at least 9%, of at least 10%, of at least 11%, of at least 12%, of at least 13%, of at least 14%, of at least 15%, of at least 16% or of at least 17% by weight, based on the total weight of said aqueous alkaline solution, and of at most 50%, of at most 48%, of at most 46%, of at most 44%, of at most 42%, of at most 40%, of at most 38%, of at most 36%, of at most 34%, of at most 32%, of at most 30%, of at most 28%, of at most 26%, of at most 24%, of at most 22% by weight, based on the total weight of said aqueous alkaline solution.

Said neutralized stream formed in stage b6) preferably comprises 2,3,3,3-tetrafluoropropene (HFO-1234yf), a portion of said part of the intermediate products B and a portion of said part of the byproducts C. Preferably, said neutralized stream formed in stage b6) preferably comprises 2,3,3,3-tetrafluoropropene (HFO-1234yf), 1,1,1,2,2-pentafluoropropane (HFC-245cb) and trans-1,3,3,3-tetrafluoro-1-propene (HFO-1234zeE).

The content of hydrofluoric acid in said neutralized stream is less than the content of hydrofluoric acid of said stream G1c", before it is neutralized. Said neutralized stream formed in stage b6) can also contain water.

Said neutralized stream formed in stage b6) can thus be dried in stage b7) of the present process. Preferably, said neutralized stream formed in stage b6) is dried over a molecular sieve. For example, said neutralized stream formed in stage b6) is dried over a 3 A molecular sieve, such as siliporite.

Stage b7) of the present process makes possible the formation of a neutralized and dried stream G1c'''' comprising 2,3,3,3-tetrafluoropropene (HFO-1234yf), a portion of said part of the intermediate products B and a portion of said part of the byproducts C. Said stream G1c'''' can optionally be compressed and liquefied at a pressure of at most 8 bara in order to form a compressed stream in which 2,3,3,3-tetrafluoropropene (HFO-1234yf), a portion of said part of the intermediate products B and a portion of said part of the byproducts C are in the liquid form.

According to a preferred embodiment, the liquid phase resulting from the mixing of said liquid phase of the stream G1c' and of the stream G1c''' is recycled in stage b3). The liquid phase resulting from the mixing of said liquid phase of the stream G1c' and of the stream G1c''' can have a concentration of hydrofluoric acid of greater than 41% by weight, based on the total weight of said liquid phase resulting from the mixing of said liquid phase of the stream G1c' and of the stream G1c'''. Advantageously, said liquid phase resulting from the mixing of said liquid phase of the stream G1c' and of the stream G1c''' can have a concentration of hydrofluoric acid of greater than 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95% by weight, based on the total weight of said liquid phase resulting from the mixing of said liquid phase of the stream G1c' and of the stream G1c'''. Preferably, said liquid phase resulting from the mixing of said liquid phase of the stream G1c' and of the stream G1c''' can have a concentration of hydrofluoric acid of between 45% and 95% by weight, between 50% and 90% by weight, between 55% and 85% by weight, between 60% and 80% by weight or between 65% and 75% by weight, based on the total weight of said liquid phase resulting from the mixing of said liquid phase of the stream G1c' and of the stream G1c'''.

According to another preferred embodiment, the liquid phase resulting from the mixing of said liquid phase of the stream G1c' and of the stream G1c''' is distilled in order to form a stream G2c, preferably at the distillation column top. Advantageously, said stream G2c comprises hydrofluoric acid containing less than 3000 ppm of water, preferably less than 2000 ppm of water, more preferably less than 1000 ppm of water, in particular less than 500 ppm of water, more particularly less than 200 ppm of water, favorably less than 100 ppm of water, more favorably less than 50 ppm of water, based on the total weight of the stream G2c. Said stream G2c can also comprise less than 50 ppm of hydrochloric acid, advantageously less than 45 ppm of hydrochloric acid, preferably less than 40 ppm of hydrochloric acid, more preferably less than 35 ppm of hydrochloric acid, in particular less than 30 ppm of hydrochloric acid, more particularly less than 20 ppm of hydrochloric acid, based on the total weight of the stream G2c. Said stream G2c can also comprise less than 50 ppm of organic compounds, advantageously less than 45 ppm of organic compounds, preferably less than 40 ppm of organic compounds, more preferably less than 35 ppm of organic compounds, in particular less than 30 ppm of organic compounds, more particularly less than 20 ppm of organic compounds, based on the total weight of the stream G2c. An organic compound is a compound comprising at least one carbon atom. The temperature at the distillation column top can be at a temperature from 10° C. to 60° C., preferably from 20° C. to 50° C.

In addition, the distillation of said liquid phase resulting from the mixing of said liquid phase of the stream G1c' and of the stream G1c''' forms a stream G3c, preferably at the distillation column bottom, comprising hydrofluoric acid in the form of an aqueous solution with a concentration of less than 50% by weight. Advantageously, said stream G3c comprising hydrofluoric acid in the form of an aqueous solution with a concentration of less than 50% by weight, 49% by weight, 48% by weight, 47% by weight, 46% by weight, 45% by weight, 44% by weight, 43% by weight, 42% by weight, based on the total weight of said stream G3c. Preferably, said stream G3c comprising hydrofluoric acid in the form of an aqueous solution with a concentration of greater than 20% by weight, based on the total weight of said stream G3c. In particular, said stream G3c comprising hydrofluoric acid in the form of an aqueous solution with a concentration of greater than 21% by weight, 22% by weight, 23% by weight, 24% by weight, 25% by weight, 26% by weight, 27% by weight, 28% by weight, 29% by weight, 30% by weight, 31% by weight, 32% by weight, 33% by weight, 34% by weight, 35% by weight, based on the total weight of said stream G3c. Said aqueous solution obtained in the stream G3c can be sold or destroyed by neutralization.

According to a preferred embodiment, the process comprises a stage c), subsequent to stage b5) or to stage b7), in which the stream G1c'' obtained in stage b5) or the stream G1c'''' obtained in stage b7) comprises 2,3,3,3-tetrafluoropropene (HFO-1234yf), 1,1,1,2,2-pentafluoropropane (HFC-245cb) and trans-1,3,3,3-tetrafluoro-1-propene (HFO-1234zeE); and said stream G1c'' or G1c'''' is distilled in order to form a stream G1e comprising 2,3,3,3-tetrafluoropropene (HFO-1234yf) and a stream G1f comprising 1,1,1,2,2-pentafluoropropane (HFC-245cb) and trans-1,3,3,3-tetrafluoro-1-propene (HFO-1234zeE).

The stream G1f obtained in stage c) can be separated by extractive distillation.

According to a specific embodiment, the stream G1f obtained in step c) is separated by extractive distillation according to the stages:
  c1) bringing said stream G1f obtained in stage c) into contact with an organic extraction agent in order to form a stream G1g, and
  c2) extractive distillation of the stream G1g in order to form a flow G1h comprising 1,1,1,2,2-pentafluoropropane (HFC-245cb), advantageously at the distillation column top, and a composition G1i comprising trans-1,3,3,3-tetrafluoro-1-propene (HFO-1234zeE) and said organic extraction agent, advantageously at the distillation column bottom.

Preferably, the stream G1i comprising trans-1,3,3,3-tetrafluoro-1-propene (HFO-1234zeE) and said organic extraction agent is separated by distillation in order to form a stream G1j comprising said organic extraction agent and a stream G1k comprising trans-1,3,3,3-tetrafluoro-1-propene (HFO-1234zeE). The stream G1j comprising said organic extraction agent can be recycled in stage c1). The stream G1k comprising trans-1,3,3,3-tetrafluoro-1-propene (HFO-1234zeE) can be either purified or destroyed by incineration.

According to a preferred embodiment, said organic extraction agent is a solvent chosen from the group consisting of halohydrocarbon, alcohol, ketone, amine, ester, ether, aldehyde, nitrile, carbonate, thioalkyl, amide and heterocycle. Advantageously, said organic extraction agent is a solvent selected from the group consisting of alcohol, ketone, amine, ester and heterocycle. According to a preferred embodiment, said organic extraction agent has a boiling point of between 10 and 150° C.

Preferably, said extraction agent can have a separation factor $S_{1,2}$ of greater than or equal to 1.1, said separation factor being calculated by the formula $S_{1,2}=(\gamma_{1,S}*P1)/(\gamma_{2,S}*P2)$, in which
  $\gamma_{1,S}$ represents the activity coefficient of 1,1,1,2,2-pentafluoropropane in said organic extraction agent at infinite dilution,
  P1 represents the saturated vapor pressure of 1,1,1,2,2-pentafluoropropane,
  $\gamma_{2,S}$ represents the activity coefficient of said trans-1,3,3,3-tetrafluoro-1-propene (HFO-1234zeE) in said organic extraction agent at infinite dilution,
  P2 represents the saturated vapor pressure of said trans-1,3,3,3-tetrafluoro-1-propene (HFO-1234zeE);
advantageously, the separation factor is greater than or equal to 1.2, preferably greater than or equal to 1.4, more preferably greater than or equal to 1.6, in particular greater than or equal to 1.8, more particularly greater than or equal to 2.0.

The saturated vapor pressure is considered for a temperature of 25° C.

Preferably, said organic extraction agent can have a separation capacity $C_{2,S}$ of greater than or equal to 0.20, said separation capacity being calculated by the formula $C_{2,S}=1/(\gamma_{2,S})$, in which $\gamma_{2,S}$ represents the activity coefficient of said trans-1,3,3,3-tetrafluoro-1-propene (HFO-1234zeE) in said organic extraction agent at infinite dilution;
advantageously, the separation capacity $C_{2,S}$ is greater than or equal to 0.40, preferably greater than or equal to 0.60, more preferably greater than or equal to 0.80, in particular greater than or equal to 1.0.

Preferably, said organic extraction agent can have a separation factor $S_{1,2}$ of greater than or equal to 1.5 and an absorption capacity $C_{2,S}$ of greater than or equal to 0.6 and be selected from the group consisting of ethylamine, acetaldehyde, isopropylamine, methyl formate, diethyl ether, 1,2-epoxypropane, ethylmethylamine, dimethoxymethane, 2-amino-2-methylpropane, methyl cyclopropyl ether, n-propylamine, isopropylmethylamine, 2-ethoxypropane, methyl t-butyl ether, diethylamine, propanone, methyl acetate, 4-methoxy-2-methyl-2-butanethiol, 2-butanamine, N-methylpropylamine, isobutanal, tetrahydrofuran, isopropyl formate, diisopropyl ether, 2-ethoxy-2-methylpropane, 1-butylamine, ethyl acetate, butanone, n-propyl formate, 2-ethoxybutane, 1-methoxy-2-methylbutane, 2,2-dimethoxypropane, 1-ethoxy-2-methylpropane, diisopropylamine, 1,2-dimethoxyethane, 3-methyl-2-butanamine, diethoxymethane, isopropyl acetate, di(n-propyl) ether, 3-pentylamine, N-methylbutylamine, 1-ethoxybutane, 1-methoxy-2-propanamine, 2-methylbutanal, 2-methoxyethanamine, tert-butyl acetate, propionitrile, 2-allyloxyethanol, 1-methoxypentane, ethyl propionate, 1,2-dimethoxypropane, 1,4-dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, dipropylamine, 2-ethoxyethanamine, sec-butyl acetate, N-methyl-1,2-ethanediamine, 2,2-diethoxypropane, pyridine, 4-methyl-2-pentanone, 1,2-diaminoethane, butyronitrile, sec-butyl tert-butyl ether, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-ethylbutylamine, diethyl carbonate, n-butyl acetate, 2-hexanone, N-ethylethylenediamine, 5-hexen-2-one, 2-methylpyridine, 2-methoxy-1-propanol, hexanal, 1-ethoxy-2-propanol, 4-methyl-2-hexanamine, hexylamine, methoxycyclohexane, 2-(dimethylamino)ethanol, cyclohexylamine, N-ethyl-2-dimethylaminoethylamine, ethoxyethanol, 2-methylpyrazine, 2-ethoxy-1-propanol, 1-methylpiperazine, 1,3-propanediamine, di(n-butyl) ether, valeronitrile, 2-heptanamine, 1-ethoxyhexane, N,N-diethylethylenediamine, 2,6-dimethylpyridine, 4-methyl-2-hexanone, 1,1,1-triethoxyethane, 1-methoxy-2-acetoxypropane, 4-methylpyridine, N,N'-diethyl-1,2-ethanediamine, 2,6-dimethylmorpholine, methyl hexanoate, 2-propoxyethanol and 1-propoxy-2-propanol. Advantageously, said organic extraction agent can have a separation factor $S_{1,2}$ of greater than or equal to 1.8 and/or an absorption capacity $C_{2,S}$ of greater than or equal to 0.8 and be selected from the group consisting of ethylamine, isopropylamine, ethylmethylamine, 2-amino-2-methylpropane, n-propylamine, isopropylmethylamine, diethylamine, propanone, 2-butanamine, N-methylpropylamine, tetrahydrofuran, 1-butylamine, ethyl acetate, butanone, 1,2-dimethoxyethane, 3-methyl-2-butanamine, 3-pentylamine, N-methylbutylamine, 1-methoxy-2-propanamine, 2-methoxyethanamine, ethyl propionate, 1,4-dioxane, 3-pentanone, 2-pentanone, 2-methoxy-1-propanamine, trimethoxymethane, n-pentylamine, 3,3-dimethyl-2-butanone, 1,3-dioxane, piperidine, 2-ethoxyethanamine, N-methyl-1,2-ethanediamine, 1,2-diaminoethane, butyronitrile, 1-methoxy-2-propanol, 1,2-propanediamine, 1-(dimethylamino)-2-propanol, 2-ethylbutylamine, diethyl carbonate, n-butyl acetate, 2-hexanone, N-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, N-ethyl-2-dimethylaminoethylamine, 2-ethoxy-1-propanol, 1-methylpiperazine, 1,3-propanediamine, valeronitrile, 2-heptanamine, N,N-diethylethylenediamine, 4-methyl-2-hexanone, 1-methoxy-2-acetoxypropane, 4-methylpyridine, N,N'-diethyl-1,2-ethanediamine, 2,6-dimethylmorpholine, methyl hexanoate, 2-propoxyethanol and 1-propoxy-2-propanol. Preferably, said organic extraction agent can have a separation factor $S_{1,2}$ of greater than or equal to 1.9 and/or an absorption capacity $C_{2,S}$ of greater than or equal to 0.9 and be selected from the group consisting of ethylamine, isopropylamine, ethylmethylamine, 2-amino-2-methylpropane, n-propylamine, isopropylmethylamine, diethylamine, propanone, 2-butanamine, N-methylpropylamine, tetrahydrofuran, 1-butylamine, ethyl acetate, butanone, 1,2-dimethoxyethane, 3-methyl-2-butanamine, 3-pentylamine, N-methylbutylamine, 1-methoxy-2-propanamine, 2-methoxyethanamine, ethyl propionate, 1,4-dioxane, 3-pentanone, 2-pentanone, 2-methoxy-1-propanamine, n-pentylamine, 3,3-dimethyl-2-butanone, 1,3-dioxane, piperidine, 2-ethoxyethanamine, N-methyl-1,2-ethanediamine, 1,2-diaminoethane, 1,2-propanediamine, 1-(dimethylamino)-2-propanol, 2-ethylbutylamine, n-butyl acetate, 2-hexanone, N-ethylethylenediamine, 1-ethoxy-2-propanol, 4-methyl-2-hexanamine, hexylamine, 2-(dimethylamino) ethanol, cyclohexylamine, N-ethyl-2-dimethylaminoethylamine, 2-ethoxy-1-propanol, 1-methylpiperazine, 1,3-propanediamine, 2-heptanamine, N,N-diethylethylenediamine, 1-methoxy-2-acetoxypropane, 4-methylpyridine, N,N'-diethyl-1,2-ethanediamine, 2,6-dimethylmorpholine, methyl hexanoate and 1-propoxy-2-propanol. More particularly, said organic extraction agent is chosen from the group consisting of ethylamine, isopropylamine, n-propylamine, diethylamine, propanone, tetrahydrofuran, ethyl acetate, butanone, 3-pentylamine, 2-methoxyethanamine, 1,4-dioxane, 3-pentanone, 2-pentanone, n-pentylamine, 1,3-dioxane, 1,2-diaminoethane, 1,2-propanediamine, 2-methoxyethanol, n-butyl acetate and 1-ethoxy-2-propanol.

Said flow G1h comprising 1,1,1,2,2-pentafluoropropane (HFC-245cb) can be recycled in stage a) of the present process.

As explained above, the stream G1i comprising trans-1,3,3,3-tetrafluoro-1-propene (HFO-1234zeE) and said organic extraction agent is distilled in order to separate the organic extraction agent from the trans-1,3,3,3-tetrafluoro-1-propene (HFO-1234zeE); advantageously, said organic extraction agent thus separated is recycled in stage c1). The trans-1,3,3,3-tetrafluoro-1-propene (HFO-1234zeE) can be incinerated or purified in order to be used subsequently or in order to be sold.

The stream G1e can be purified, for example by extractive distillation, in order to remove the trans-1,3,3,3-tetrafluoro-1-propene (HFO-1234ze-E) possibly present. In this case, said organic extraction agent is a solvent chosen from the group consisting of hydrocarbon, halohydrocarbon, alcohol, ketone, amine, ester, ether, aldehyde, nitrile, carbonate, thioalkyl, amide and heterocycle; or said organic extraction agent is difluorodiethylsilane, triethylfluorosilane or perfluorobutanoic acid; preferably from the group consisting of amine, ether, ketone, ester, alcohol, aldehyde and heterocycle. The boiling point of said organic extraction agent can be between 10 and 150° C. Said organic extraction agent can have a separation factor $S_{1,2}$ of greater than or equal to 1.1, said separation factor being calculated by the formula $S_{1,2}=(\gamma_{1,S}*P1)/(\gamma_{2,S}*P2)$, in which $\gamma_{1,S}$ represents the activity coefficient of 2,3,3,3-tetrafluoro-1-propene in said organic extraction agent at infinite dilution, P1 represents the saturated vapor pressure of 2,3,3,3-tetrafluoro-1-propene, $\gamma_{2,S}$ represents the activity coefficient of trans-1,3,3,3-tetrafluoro-1-propene (HFO-1234ze-E) in said organic extraction agent at infinite dilution and P2 represents the saturated vapor pressure of said at least one of the compounds consisting of trans-1,3,3,3-tetrafluoro-1-propene (HFO- 1234ze-E); advantageously, the separation factor is greater than or equal to 1.2, preferably greater than or equal to 1.4, more preferably greater than or equal to 1.6, in particular greater than or equal to 1.8 and more particularly greater than or equal to 2.0. Said organic extraction agent can have an absorption capacity $C_{2,S}$ of greater than or equal to 0.20, said absorption capacity being calculated by the formula $C_{2,S}=1/(\gamma_{2,S})$, in which $\gamma_{2,S}$ represents the activity coefficient of trans-1,3,3,3-tetrafluoro-1-propene (HFO-1234ze-E) in said organic extraction agent at infinite dilution; advantageously, the absorption capacity $C_{2,S}$ is greater than or equal to 0.40, preferably greater than or equal to 0.60, more preferably greater than or equal to 0.80, in particular greater than or equal to 1.0. Advantageously, said organic extraction agent can be ethylamine, isopropylamine, diethyl ether, ethoxyethene, dimethoxymethane, n-propylamine, methyl t-butyl ether, diethylamine, propanone, methyl acetate, isobutanal, tetrahydrofuran, isopropyl formate, diisopropyl ether, 2-ethoxy-2-methylpropane, ethyl acetate, butanone, diethoxymethane, isopropyl acetate, 3-pentylamine, 2-methoxyethanamine, tert-butyl acetate, 1,4-dioxane, 3-pentanone, 1,1-diethoxyethane, 2-pentanone, trimethoxymethane, n-pentylamine, 1,3-dioxane, 3,3-dimethyl-2-butanone, sec-butyl acetate, 4-methyl-2-pentanone, 1,2-diaminoethane, 1-methoxy-2-propanol, diethyl carbonate, n-butyl acetate, 1-ethoxy-2-propanol or hexanal; advantageously, said organic extraction agent is chosen from the group consisting of ethylamine, isopropylamine, diethyl ether, dimethoxymethane, n-propylamine, diethylamine, diisopropyl ether, 2-ethoxy-2-methylpropane, butanone, diethoxymethane, isopropyl acetate, 3-pentylamine, 2-methoxyethanamine, tert-butyl acetate, 1,4-dioxane, trimethoxymethane, n-pentylamine, 1,3-dioxane, sec-butyl acetate, 1,2-diaminoethane, 1-methoxy-2-propanol, n-butyl acetate, 1-ethoxy-2-propanol and hexanal; preferably, said organic extraction agent is chosen from the group consisting of ethylamine, isopropylamine, diethyl ether, dimethoxymethane, n-propylamine, diethylamine, diisopropyl ether, 2-ethoxy-2-methylpropane, diethoxymethane, isopropyl acetate, 3-pentylamine, 2-methoxyethanamine, tert-butyl acetate, 1,4-dioxane, trimethoxymethane, n-pentylamine, 1,3-dioxane, sec-butyl acetate, 1,2-diaminoethane, 1-methoxy-2-propanol, n-butyl acetate, 1-ethoxy-2-propanol and hexanal.

Alternatively, the process comprises a stage c), subsequent to stage b5) or to stage b7), in which the stream G1c'' obtained in stage b5) or the stream G1c'''' obtained in stage b7) comprises 2,3,3,3-tetrafluoropropene (HFO-1234yf), 1,1,1,2,2-pentafluoropropane (HFC-245cb) and trans-1,3,3,3-tetrafluoro-1-propene (HFO-1234zeE); and said stream G1c'' or G1c'''' is distilled in order to form a stream G1e' comprising 2,3,3,3-tetrafluoropropene (HFO-1234yf) and 1,1,1,2,2-pentafluoropropane (HFC-245cb) and a stream G1f' comprising trans-1,3,3,3-tetrafluoro-1-propene (HFO-1234zeE); advantageously, the stream G1c'' or G1c'''' is distilled by extractive distillation.

According to a preferred embodiment, the stream G1c'' or G1c'''' is distilled by extractive distillation following the stages:
c1') bringing said stream G1c'' or G1c'''' into contact with an organic extraction agent in order to form a stream G1g', and
c2') extractive distillation of the stream G1g' in order to form the flow G1e' comprising 2,3,3,3-tetrafluoropropene (HFO-1234yf) and 1,1,1,2,2-pentafluoropropane (HFC-245cb), advantageously at the distillation column top, and the stream G1h' comprising trans-1,3,3,3-tetrafluoro-1-propene (HFO-1234zeE) and said organic extraction agent, advantageously at the distillation column bottom.

According to a preferred embodiment, said organic extraction agent can have a separation factor $S_{1,2}$ of greater than or equal to 1.1, said separation factor being calculated by the formula $S_{1,2}=(\gamma_{1,S}*P1)/(\gamma_{2,S}*P2)$, in which $\gamma_{1,S}$ represents the activity coefficient of 2,3,3,3-tetrafluoro-1-propene in said organic extraction agent at infinite dilution, P1 represents the saturated vapor pressure of 2,3,3,3-tetrafluoro-1-propene, $\gamma_{2,S}$ represents the activity coefficient of trans-1,3,3,3-tetrafluoro-1-propene (HFO-1234ze-E) in said organic extraction agent at infinite dilution and P2 represents the saturated vapor pressure of trans-1,3,3,3-tetrafluoro-1-propene (HFO-1234ze-E); advantageously, the separation factor is greater than or equal to 1.2, preferably greater than or equal to 1.4, more preferably greater than or equal to 1.6 and in particular greater than or equal to 1.8. In this embodiment, said organic extraction agent can also have a separation factor $S_{1,2}$ of greater than or equal to 1.1, said separation factor being calculated by the formula $S_{1,2}=(\gamma_{1,S}*P1)/(\gamma_{2,S}*P2)$, in which $\gamma_{1,S}$ represents the activity coefficient of 1,1,1,2,2-pentafluoropropane (HFC-245cb) in said organic extraction agent at infinite dilution, P1 represents the saturated vapor pressure of 1,1,1,2,2-pentafluoropropane (HFC-245cb), $\gamma_{2,S}$ represents the activity coefficient of trans-1,3,3,3-tetrafluoro-1-propene (HFO-1234ze-E) in said organic extraction agent at infinite dilution and P2 represents the saturated vapor pressure of trans-1,3,3,3-tetrafluoro-1-propene (HFO-1234ze-E); advantageously, the separation factor is greater than or equal to 1.2, preferably greater than or equal to 1.4, more preferably greater than or equal to 1.6, in particular greater than or equal to 1.8 and more particularly greater than or equal to 2.0. In this preferred embodiment, said organic extraction agent can have an absorption capacity $C_{2,S}$ of greater than or equal to 0.20, said absorption capacity being calculated by the formula $C_{2,S}=1/(\gamma_{2,S})$, in which $\gamma_{2,S}$ represents the activity coefficient of said at least one of the compounds consisting of trans-1,3,3,3-tetrafluoro-1-propene (HFO-1234ze-E) in said organic extraction agent at infinite dilution; preferably, $\gamma_{2,S}$ represents the activity coefficient of said at least one of the compounds consisting of trans-1,3,3,3-tetrafluoro-1-propene (HFO-1234ze-E) in said organic extraction agent at infinite dilution; advantageously, the absorption capacity $C_{2,S}$ is greater than or equal to 0.40, preferably greater than or equal to 0.60, more preferably greater than or equal to 0.80, in particular greater than or equal to 1.0. Thus, in this preferred embodiment, said organic extraction agent can be ethylamine, isopropylamine, diethyl ether, ethylmethylamine, 2-amino-2-methylpropane, n-propylamine, isopropylmethylamine, 2-ethoxypropane, methyl t-butyl ether, diethylamine, propanone, methyl acetate, 2-butanamine, N-methylpropylamine, isobutanal, tetrahydrofuran, 1-butylamine, ethyl acetate, butanone, n-propyl formate, 2,2-dimethoxypropane, 1-ethoxy-2-methylpropane, 1,2-dimethoxyethane, 3-methyl-2-butanamine, diethoxymethane, isopropyl acetate, 3-pentylamine, N-methylbutylamine, 1-ethoxybutane, 1-methoxy-2-propanamine, 2-methylbutanal, 2-methoxyethanamine, tert-butyl acetate, 1-methoxypentane, ethyl propionate, 1,2-dimethoxypropane, 1,4-dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, N-methyl-1,2-ethanediamine, 2,2-diethoxypropane, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, 1,1-diethoxypropane, 2-ethylbutylamine, diethyl carbonate, n-butyl acetate, 2-hexanone, N-ethylethylenediamine, 5-hexen-2-one, 2-methylpyridine, 2-methoxy-1-propanol or hexanal; advantageously ethylamine, isopropylamine, diethyl ether, n-propylamine, diethylamine, propanone, methyl acetate, butanone, diethoxymethane, isopropyl acetate, 3-pentylamine, 2-methoxyethanamine, tert-butyl acetate, 1,4-dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol or hexanal; preferably ethylamine, isopropylamine, diethyl ether, n-propylamine, diethylamine, diethoxymethane, isopropyl acetate, 3-pentylamine, 2-methoxyethanamine, tert-butyl acetate, 1,4-dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol or hexanal.

Preferably, the stream G1e' comprising 2,3,3,3-tetrafluoropropene (HFO-1234yf) and 1,1,1,2,2-pentafluoropropane (HFC-245cb) can be subjected to subsequent purification stages. Thus, the 2,3,3,3-tetrafluoropropene (HFO-1234yf) can be separated, preferably by distillation, from the 1,1,1,2,2-pentafluoropropane (HFC-245cb) in order to form a stream comprising 2,3,3,3-tetrafluoropropene (HFO-1234yf) and a stream G1i' comprising 1,1,1,2,2-pentafluoropropane (HFC-245cb), said stream G1i' being recycled in stage a). The 2,3,3,3-tetrafluoropropene (HFO-1234yf) can also be subjected to subsequent purification stages in order to obtain a degree of purity sufficient for its marketing. For example, it can be purified, for example by extractive distillation, in order to remove trans-1,3,3,3-tetrafluoro-1-propene (HFO-1234ze-E) possibly present.

Preferably, the stream G1h' comprising trans-1,3,3,3-tetrafluoro-1-propene (HFO-1234zeE) and said organic extraction agent is separated by distillation in order to form a stream G1j' comprising said organic extraction agent and a stream G1k' comprising trans-1,3,3,3-tetrafluoro-1-propene (HFO-1234zeE). The stream G1j' comprising said organic extraction agent can be recycled in stage c1'). The stream G1k' comprising trans-1,3,3,3-tetrafluoro-1-propene (HFO-1234zeE) can be either purified or destroyed by incineration.

Optionally or not, if the stream G1c comprises impurities having a lower boiling point than that of 2,3,3,3-tetrafluoro-1-propene, they can be removed by distillation. Said impurities having a lower boiling point than that of 2,3,3,3-tetrafluoro-1-propene can be trifluoromethane (HFC-23), monofluoromethane (HFC-41), difluoromethane (HFC-32), pentafluoroethane (HFC-125), 1,1,1-trifluoroethane (HFC-143a), trifluoropropyne or 1-chloropentafluoroethane (CFC-115), and these impurities can be recovered at the distillation column top. The stream recovered at the distillation column bottom can subsequently be used as described above for the stream G1c in stage b) and the subsequent stages.

According to another preferred embodiment, said liquid stream L1 comprises all or part of the intermediate products B and all or part of the byproducts C, and all or part of this stream L1 is brought to low temperature, advantageously between −50° C. and 20° C., in order to form a first phase L1a comprising a part of the unreacted HF and a second phase L1b comprising said intermediate products B and said byproducts C. Thus, said liquid stream L1 can comprise a part of the intermediate products B and a part of the byproducts C, and all or part of this stream L1 is brought to low temperature, advantageously between −50° C. and 20° C., in order to form a first phase L1a comprising a part of the unreacted HF and a second phase L1b comprising said intermediate products B and said byproducts C. Advantageously, said low temperature is between −50° C. and 15° C., preferably between −40° C. and 10° C., in particular between −30° C. and 0° C. This stage can be carried out continuously or batchwise.

Said first phase L1a can be recycled in stage a).

Optionally or not, said stream G1d formed in stage b2) can be mixed with the liquid stream L1 before all or part of the latter is brought to low temperature.

All or part of the 1,1,1,2,2-pentafluoropropane (HFC-245cb) can also be contained in said liquid stream L1 and then in said second phase L1b.

All or part of the 1,3,3,3-tetrafluoro-1-propene (HFO-1234ze) can also be contained in said liquid stream L1 and then in said second phase L1b.

All or part of the 2-chloro-3,3,3-trifluoropropene (HCFO-1233xf) can also be contained in said liquid stream L1 and then in said second phase L1b.

All or part of the E-1-chloro-3,3,3-trifluoro-1-propene (HCFO-1233zdE) can also be contained in said liquid stream L1 and then in said second phase L1b.

All or part of the 1,1,1,3,3-pentafluoropropane (HFC-245fa) can also be contained in said liquid stream L1 and then in said second phase L1b.

Preferably, said second phase L1b can comprise 1,1,1,3,3-pentafluoropropane (HFC-245fa), E-1-chloro-3,3,3-trifluoro-1-propene (HCFO-1233zdE), 2-chloro-3,3,3-trifluoropropene (HCFO-1233xf), 1,3,3,3-tetrafluoro-1-propene (HFO-1234ze) and 1,1,1,2,2-pentafluoropropane (HFC-245cb).

According to a preferred embodiment, said second phase L1b is distilled in order to recover a stream L1c comprising 1,1,1,2,2-pentafluoropropane (HFC-245cb) and 1,3,3,3-tetrafluoro-1-propene (HFO-1234ze), advantageously at the distillation column top, and a stream L1d comprising 2-chloro-3,3,3-trifluoro-1-propene (HCFO-1233xf), E-1-chloro-3,3,3-trifluoro-1-propene (HCFO-1233zdE) and 1,1,1,3,3-pentafluoropropane (HFC-245fa), advantageously at the distillation column bottom. Said stream L1c can be recycled in stage a). Optionally, said stream L1c can be purified in order to separate 1,1,1,2,2-pentafluoropropane (HFC-245cb) and 1,3,3,3-tetrafluoro-1-propene (HFO-1234ze). This can be carried out by extractive distillation as explained above in connection with the separation of the stream G1f.

According to a preferred embodiment, said stream L1d can be separated in order to form a flow comprising 2-chloro-3,3,3-trifluoro-1-propene (HCFO-1233xf) and a stream comprising E-1-chloro-3,3,3-trifluoro-1-propene (HCFO-1233zdE) and 1,1,1,3,3-pentafluoropropane (HFC-245fa). The separation of said stream L1d can be carried out by extractive distillation.

Preferably, said stream L1d can be an azeotropic or quasi-azeotropic composition comprising 2-chloro-3,3,3-trifluoro-1-propene (HCFO-1233xf), E-1-chloro-3,3,3-trifluoro-1-propene (HCFO-1233zdE) and 1,1,1,3,3-pentafluoropropane (HFC-245fa).

Preferably, said separation can be carried out by extractive distillation. Said extractive distillation of said stream L1d comprises the stages of:
bringing said stream L1d into contact with an organic extraction agent in order to form a composition L1e, and extractive distillation of the composition L1e in order to form a flow L1f comprising 2-chloro-3,3,3-trifluoro-1-propene (HCFO-1233xf), advantageously at the distillation column top, and a stream L1g comprising E-1- chloro-3,3,3-trifluoro-1-propene (HCFO-1233zdE) and 1,1,1,3,3-pentafluoropropane (HFC-245fa) and said organic extraction agent, advantageously at the distillation column bottom.

Preferably, the stream L1g is subsequently separated by distillation in order to form a stream L1h comprising said organic extraction agent and a stream L1i comprising E-1-chloro-3,3,3-trifluoro-1-propene (HCFO-1233zdE) and 1,1,1,3,3-pentafluoropropane (HFC-245fa). The stream L1h can be recycled in order to be brought into contact with a stream L1d in order to form a composition L1e. The stream L1i comprising E-1-chloro-3,3,3-trifluoro-1-propene (HCFO-1233zdE) and 1,1,1,3,3-pentafluoropropane (HFC-245fa) can be either purified or destroyed by incineration.

According to a preferred embodiment, said organic extraction agent brought into contact with the stream L1d is a solvent chosen from the group consisting of hydrocarbon, halohydrocarbon, alcohol, ketone, amine, ester, ether, aldehyde, nitrile, carbonate, sulfoxide, sulfate, thioalkyl, amide, heterocycle and phosphate or the organic extraction agent is perfluorobutanoic acid. According to a preferred embodiment, said organic extraction agent has a boiling point of between 50 and 200° C. According to a preferred embodiment, said organic extraction agent has a separation factor $S_{1,2}$ of greater than or equal to 1.1, said separation factor being calculated by the formula $S_{1,2}=(\gamma_{1,S}*P1)/(\gamma_{2,S}*P2)$, in which $\gamma_{1,S}$ represents the activity coefficient of 2-chloro-3,3,3-trifluoropropene in said organic extraction agent at infinite dilution, P1 represents the saturated vapor pressure of 2-chloro-3,3,3-trifluoropropene, $\gamma_{2,S}$ represents the activity coefficient of 1,1,1,3,3-pentafluoropropane (HFC-245fa) in said organic extraction agent at infinite dilution, P2 represents the saturated vapor pressure of 1,1,1,3,3-pentafluoropropane (HFC-245fa);

advantageously, the separation factor $S_{1,2}$ is greater than or equal to 1.2, preferably greater than or equal to 1.4, more preferably greater than or equal to 1.6, in particular greater than or equal to 1.8, more particularly greater than or equal to 2.0;

and said organic extraction agent has an absorption capacity $C_{2,S}$ of greater than or equal to 0.20, said absorption capacity being calculated by the formula $C_{2,S}=1/(\gamma_{2,S})$, in which $\gamma_{2,S}$ represents the activity coefficient of 1,1,1,3,3-pentafluoropropane (HFC-245fa) in said organic extraction agent at infinite dilution; advantageously, the absorption capacity $C_{2,S}$ is greater than or equal to 0.40, preferably greater than or equal to 0.60, more preferably greater than or equal to 0.80, in particular greater than or equal to 1.0.

Thus, according to a specific embodiment, said organic extraction agent can be chosen from the group consisting of ethanedial, propanone, methyl acetate, methylglyoxal, ethyl acetate, butanone, propionitrile, 1,4-dioxane, trimethoxymethane, 1,3-dioxane, 1,3,5-trioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, methyl acetoacetate, N,N-dimethylpropanamide, dimethyl malonate, diethyl sulfoxide, 2-(2-methoxyethoxy)ethanol, trimethyl phosphate and diethyl malonate; preferably, said organic extraction agent can be chosen from the group consisting of propanone, methyl acetate, ethyl acetate, butanone, 1,4-dioxane, trimethoxymethane, 1,3-dioxane, 1,3,5-trioxane, 1,2-diaminoethane and 1-methoxy-2-propanol. Preferably, this specific embodiment can make it possible to efficiently separate 2-chloro-3,3,3-trifluoropropene and 1,1,1,3,3-pentafluoropropane (HFC-245fa).

According to a specific embodiment, said organic extraction agent brought into contact with the stream L1d can have a separation factor $S_{1,2}$ of greater than or equal to 1.1, said separation factor being calculated by the formula $S_{1,2}=(\gamma_{1,S}*P1)/(\gamma_{2,S}*P2)$, in which $\gamma_{1,S}$ represents the activity coefficient of 2-chloro-3,3,3-trifluoropropene in said organic extraction agent at infinite dilution, P1 represents the saturated vapor pressure of 2-chloro-3,3,3-trifluoropropene, $\gamma_{2,S}$ represents the activity coefficient of E-1-chloro-3,3,3-trifluoro-1-propene (HCFO-1233zdE) in said organic extraction agent at infinite dilution, P2 represents the saturated vapor pressure of E-1-chloro-3,3,3-trifluoro-1-propene (HCFO-1233zdE);

advantageously, the separation factor $S_{1,2}$ is greater than or equal to 1.2, preferably greater than or equal to 1.4, more preferably greater than or equal to 1.6, in particular greater than or equal to 1.8, more particularly greater than or equal to 2.0;

and said organic extraction agent can have an absorption capacity $C_{2,S}$ of greater than or equal to 0.20, said absorption capacity being calculated by the formula $C_{2,S}=1/(\gamma_{2,S})$, in which $\gamma_{2,S}$ represents the activity coefficient of E-1-chloro-3,3,3-trifluoro-1-propene (HCFO-1233zdE) in said organic extraction agent at infinite dilution; advantageously, the absorption capacity $C_{2,S}$ is greater than or equal to 0.40, preferably greater than or equal to 0.60, more preferably greater than or equal to 0.8, in particular greater than or equal to 1.0.

Thus, in a specific embodiment, said organic extraction agent can be chosen from the group consisting of isopropylmethylamine, methyl t-butyl ether, diethylamine, propanone, methyl acetate, 2-butanamine, N-methylpropylamine, tetrahydrofuran, 1-butylamine, ethyl acetate, butanone, n-propyl formate, dimethoxypropane, diisopropylamine, 1,2-dimethoxyethane, 3-methyl-2-butanamine, diethoxymethane, isopropyl acetate, 3-pentylamine, N-methylbutylamine, 1-methoxy-2-propanamine, 2-methoxyethanamine, tert-butyl acetate, ethyl propionate, 1,2-dimethoxypropane, 1,4-dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, N-methyl-1,2-ethanediamine, 2,2-diethoxypropane, 1,2-diaminoethane, 1-methoxy-2-propanol, 1,2-propanediamine, 2,6-dimethyl-5-heptenal, 1-(dimethylamino)-2-propanol, 3-methyl-3-pentanol, 2-ethylbutylamine, diethyl carbonate, n-butyl acetate, 2-hexanone, N-ethylethylenediamine, 2-methoxy-1-propanol, 1-ethoxy-2-propanol, 4-methyl-2-hexanamine, hexylamine, methoxycyclohexane, 2-(dimethylamino)ethanol, cyclohexylamine, N-ethyl-2-dimethylaminoethylamine, ethoxyethanol, 2-ethoxy-1-propanol, 1-methylpiperazine, 1,3-propanediamine, 2-heptanamine, N,N-diethylethylenediamine, 4-methyl-2-hexanone, 1,1,1-triethoxyethane, 1-methoxy-2-acetoxypropane, 4-methylpyridine, N,N'-diethyl-1,2-ethanediamine, 2,6-dimethylmorpholine, methyl hexanoate, 2-propoxyethanol, 1-propoxy-2-propanol, 2-heptanone, dimethylformamide, 2-isopropoxyethanol, 2-methylpiperazine, cyclohexanone, 1-heptanamine, 2-ethoxyethyl acetate, 1,4-butanediamine, 2,4-dimethylpyridine, 2-methoxy-3-methylpyrazine, 4-methoxy-4-methylpentan-2-one, 3-ethoxy-1-propanol, 3-methoxy-1-butanol, diglyme, 2-(diethylamino)ethanol, 2,2-diethoxyethanamine, 2-methoxy-N-(2-methoxyethyl)ethanamine, 2-(ethylamino) ethanol, 3-octanone, diacetone alcohol, diethylaminopropylamine, 2-ethylhexylamine, 1-butoxy-2-propanol, 2-butoxyethanol, 2-octanone, methyl heptanoate, triethylenediamine, N,N-dimethylpropanamide, 2-propyl 1-methoxypropanoate, 1,5-pentanediamine, cycloheptanone, 3,4-dimethylpyridine, 1-octanamine, benzylmethylamine, 1,1,3,3-tetramethoxypropane, dihexyl phthalate, diethylpropanolamine, 2-butoxyethyl acetate, diethyl sulfoxide, 2-(2-methoxyethoxy)ethanol, 4-methylbenzenemethanamine, diethylene glycol monoethyl ether, 2-propylcyclohexanone, trimethyl phosphate, 2-methyl-2,4-pentanediol, methyl benzoate, diethyl malonate and 2-methoxypyrimidine; preferably, said organic extraction agent is chosen from the group consisting of diethylamine, propanone, methyl acetate, tetrahydrofuran, ethyl acetate, butanone, diethoxymethane, isopropyl acetate, tert-butyl acetate, 1,4-dioxane, 3-pentanone, 1,1-diethoxyethane, 2-pentanone, n-pentylamine, 1,3-dioxane, sec-butyl acetate, 1,2-diaminoethane, 1-methoxy-2-propanol, n-butyl acetate and 1-ethoxy-2-propanol. Preferably, this specific embodiment can make it possible to efficiently separate 2-chloro-3,3,3-trifluoropropene and E-1-chloro-3,3,3-trifluoro-1-propene (HCFO-1233zdE).

According to a preferred embodiment, in order to promote the simultaneous removal of E-1-chloro-3,3,3-trifluoro-1-propene (HCFO-1233zdE) and 1,1,1,3,3-pentafluoropropane (HFC-245fa), said organic extraction agent brought into contact with the stream L1d can be selected from the group consisting of propanone, methyl acetate, ethyl acetate, butanone, 1,4-dioxane, trimethoxymethane, 1,3-dioxane, 1,2-diaminoethane, 1-methoxy-2-propanol, diethyl carbonate, 2-methoxy-1-propanol, 1-methoxy-2-acetoxypropane, dimethylformamide, 3-methoxy-1-butanol, diacetone alcohol, N,N-dimethylpropanamide, diethyl sulfoxide, 2-(2-methoxyethoxy)ethanol, trimethyl phosphate and diethyl malonate. In particular, said organic extraction agent can be selected from the group consisting of propanone, methyl acetate, ethyl acetate, butanone, 1,4-dioxane, trimethoxymethane, 1,3-dioxane, 1,2-diaminoethane, 1-methoxy-2-propanol, 3-methoxy-1-butanol and diacetone alcohol.

According to a preferred embodiment, said stream L1g comprising E-1-chloro-3,3,3-trifluoro-1-propene (HCFO-1233zdE), 1,1,1,3,3-pentafluoropropane (HFC-245fa) and said organic extraction agent can be distilled in order to separate, on the one hand, said organic extraction agent and, on the other hand, E-1-chloro-3,3,3-trifluoro-1-propene (HCFO-1233zdE) and 1,1,1,3,3-pentafluoropropane (HFC-245fa). Preferably, said organic extraction agent can be recycled.

According to a preferred embodiment, the flow L1f comprising 2-chloro-3,3,3-trifluoro-1-propene (HCFO-1233xf) is recycled in stage a).

If heavy impurities are present in said stream L1d, the latter can be distilled prior to its separation in order to remove them. The stream L1d as described above can be recovered at the distillation column top, the heavy impurities being recovered at the distillation column bottom. The heavy impurities can contain, for example, 1,2-dichloro-3,3,3-trifluoropropene (HCFO-1223xd), cis-1-chloro-3,3,3-trifluoropropene, 2-chloro-1,1,1,3,3-pentafluoropropane, 2-chloro-1,3,3,3-tetrafluoropropene and compounds of formula (I).

More particularly, the starting composition can comprise 1,1,2,3-tetrachloropropene, 2,3,3,3-tetrachloropropene, 1,1,1,2,3-pentachloropropane, 1,1,2,2,3-pentachloropropane, 1,2-dichloro-3,3,3-trifluoropropane, 2-chloro-2,3,3,3-tetrafluoropropane, 1,1,1,2,2-pentafluoropropane and 1,1,1,3,3-pentafluoropropane, preferably 1,1,1,2,3-pentachloropropane, 1,1,2,3-tetrachloropropene, 1,1,1,2,2-pentafluoropropane and/or 2-chloro-3,3,3-trifluoro-1-propene, 1,2-dichloro-3,3,3-trifluoropropane; in particular 1,1,1,2,3-pentachloropropane (HCC-240db).

The catalyst used in the present process for the production of 2,3,3,3-tetrafluoropropene can be based, for example, on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments), chromium fluorides and their mixtures. Other possible catalysts are catalysts supported on carbon, antimony-based catalysts or aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or a supported or nonsupported catalyst containing a metal such as Cr, Ni, Fe, Zn, Ti, V, Zr, Mo, Ge, Sn, Pb, Mg or Sb.

Reference may be made, in this regard, to the document WO 2007/079431 (on p. 7, l. 1-5 and 28-32), to the document EP 939 071 (section [0022]), to the document WO 2008/054781 (on p. 9, l. 22-p. 10, l. 34) and to the document WO 2008/040969 (claim 1), to which documents reference is expressly made.

The catalyst is more particularly preferably chromium-based and it is more particularly a mixed catalyst comprising chromium.

According to one embodiment, a mixed catalyst comprising chromium and nickel is used. The Cr/Ni molar ratio (on the basis of the metal element) is generally from 0.5 to 5, for example from 0.7 to 2, for example approximately 1. The catalyst can contain from 0.5% to 20% by weight of nickel.

The metal can be present in metallic form or in the form of a derivative, for example an oxide, halide or oxyhalide. These derivatives are preferably obtained by activation of the catalytic metal.

The support is preferably formed with aluminum, for example alumina, activated alumina or aluminum derivatives, such as aluminum halides and aluminum oxyhalides, for example described in the document U.S. Pat. No. 4,902,838, or obtained by the activation process described above.

The catalyst can comprise chromium and nickel in an activated or nonactivated form, on a support which has or has not been subjected to an activation.

Reference may be made to the document WO 2009/118628 (in particular on p. 4, l. 30-p. 7, l. 16), to which reference is expressly made here.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to an activation with air, oxygen or chlorine and/or with HF.

For example, the catalyst is preferably subjected to an activation with air or oxygen and HF at a temperature of 100 to 500° C., preferably of 250 to 500° C. and more particularly of 300 to 400° C. The activation time is preferably from 1 to 200 h and more particularly from 1 to 50 h.

This activation can be followed by a final stage of fluorination activation in the presence of an oxidizing agent, of HF and of organic compounds.

The HF/organic compounds molar ratio is preferably from 2 to 40 and the oxidizing agent/organic compounds molar ratio is preferably from 0.04 to 25. The temperature of the final activation is preferably from 300 to 400° C. and its duration is preferably from 6 to 100 h.

The gas-phase fluorination reaction can be carried out:
- with an HF/compound of formula (I) and/or (II) molar ratio from 3:1 to 150:1, preferably from 4:1 to 125:1 and more particularly preferably from 5:1 to 100:1;
- with a contact time of 3 to 100 s, preferably 4 to 75 s and more particularly 5 to 50 s (volume of catalyst divided by the total incoming flow, adjusted to the operating temperature and pressure);
- at a pressure ranging from atmospheric pressure to 20 bara, preferably from 2 to 18 bara and more particularly from 3 to 15 bara;
- at a temperature (temperature of the catalytic bed) of 200 to 450° C., preferably of 250 to 400° C. and more particularly of 280 to 380° C.

The duration of the reaction stage is typically from 10 to 8000 hours, preferably from 50 to 5000 hours and more particularly preferably from 70 to 1000 hours.

An oxidizing agent, preferably oxygen, can optionally be added during the fluorination reaction. The oxygen/organic compounds molar ratio can be from 0.005 to 2, preferably from 0.01 to 1.5. Oxygen can be introduced in the pure form or in the form of air or of an oxygen/nitrogen mixture. Oxygen can also be replaced with chlorine.

FIG. 1 diagrammatically illustrates a device which implements a process for the production of 2,3,3,3-tetrafluoropropene according to a specific embodiment of the present invention. Hydrofluoric acid 1 is brought into contact with 1,1,1,2,3-pentachloropropane (HCC-240db) 2 in one or more reactors 3. The mixture A obtained comprises HCl, unreacted HF, 2,3,3,3-tetrafluoropropene (HFO-1234yf), 2-chloro-3,3,3-trifluoropropene (HCFO-1233xf), 1,1,1,2,2-pentafluoropropane (HFC-245cb), trans-1,3,3,3-tetrafluoro-1-propene (HFO-1234zeE), trans-1-chloro-3,3,3-trifluoro-1-propene (HCFO-1233zdE), cis-1-chloro-3,3,3-trifluoro-1-propene (HCFO-1233zdZ), cis-1,3,3,3-tetrafluoro-1-propene (HFO-1234zeZ), 1,1,1,3,3-pentafluoropropane (HFC-245fa), 2-chloro-1,1,1,3,3-pentafluoropropane (HCFC-235da), 1,2-dichloro-3,3,3-trifluoropropane (HCFO-1223xd), 2-chloro-1,3,3,3-tetrafluoropropene (HCFO-1224xe), 1,1,1,3,3,3-hexafluoropropane (HFC-236fa) and optionally one or more compounds of formula (II) $C_nH_xF_yCl_z$ in which n=4, 5 or 6, x is an integer from 0 to 6, y is an integer from 4 to 12, z is an integer from 0 to 6, with 2n=x+y+z if w is 1 or 2n−2=x+y+z if w is 2 or 2n+2=x+y+z if w=0, w being the number of unsaturations in the compound of formula (II) considered. The mixture A is recovered at the reactor outlet and conveyed to a distillation column 5 via the pipe 4. The liquid stream L1 obtained at the distillation column 5 bottom is conveyed, either partially or completely, to the purification device 13 via the pipe 17. The gas stream G1 obtained at the distillation column 5 top is conveyed to the purification device 7 via the pipe 6. From the purification device 7, a stream comprising 2,3,3,3-tetrafluoro-1-propene is recovered at 11 via the pipe 8. A flow comprising 1,1,1,2,2-pentafluoropropane (HFC-245cb) and possibly trans-1,3,3,3-tetrafluoro-1-propene (HFO-1234zeE) is also obtained and recycled to the reactor 3 via the pipe 10. Said flow comprising 1,1,1,2,2-pentafluoropropane (HFC-245cb) and possibly trans-1,3,3,3-tetrafluoro-1-propene (HFO-1234zeE), contained in the pipe 10, can optionally be mixed with the stream L1 originating from the pipe 15 or 17 before being injected into the reactor 3. Finally, a stream comprising trans-1,3,3,3-tetrafluoro-1-propene (HFO-1234zeE) can be recovered at 12 via the pipe 9.

Figure 2:
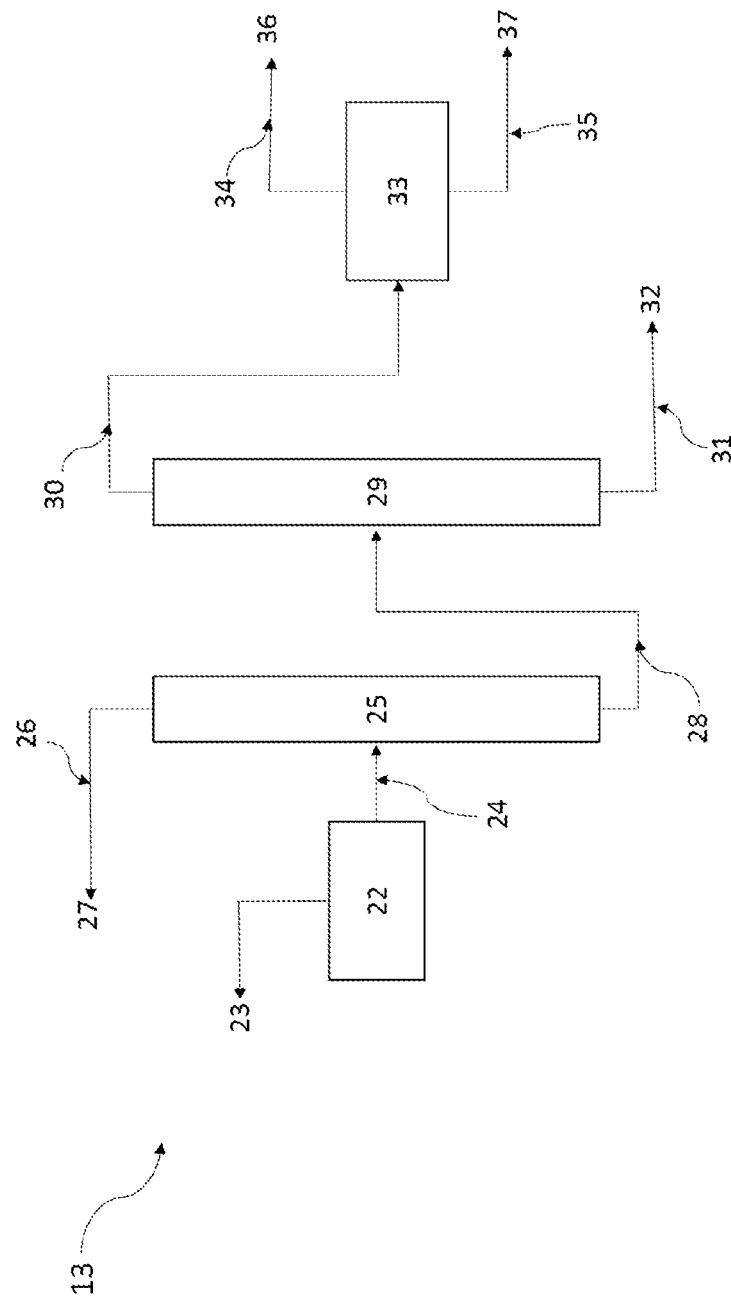
FIGS. 2, 3a, 3b and 3c diagrammatically represent a part of the device which implements the purification of 2,3,3,3-tetrafluoro-1-propene according to another specific embodiment of the present invention.

FIG. 2 diagrammatically illustrates, according to a specific embodiment of the present invention, a purification device 13. A liquid stream L1 obtained at the distillation column 5 bottom (FIG. 1) is conveyed to the settling tank 22 having a temperature of −25° C. The stream L1a is extracted and recovered at 23 in order to be recycled to the reactor 3. The stream L1b is conveyed to the distillation column 25 via the pipe 24. The stream L1c is discharged at the distillation column top and recovered at 27 via the pipe 26. It can be recovered in order to be recycled to the reactor 3. The stream L1d can be conveyed to the distillation column 29 via the pipe 28 in order to extract, at the distillation column bottom, heavy impurities possibly present and to convey them to an incinerator 32 via the pipe 31. The 2-chloro-3,3,3-trifluoropropene (HCFO-1233xf), E-1-chloro-3,3,3-trifluoro-1-propene (HCFO-1233zdE) and 1,1,1,3,3-pentafluoropropane (HFC-245fa) recovered at the top of the distillation column 29 are conveyed to a purification device 33 via the pipe 30. From this purification device 33, 2-chloro-3,3,3-trifluoropropene (HCFO-1233xf) can be extracted at 36 via the pipe 34 and be recycled to the reactor 3. The purification device 33 can be an extractive distillation. E-1-Chloro-3,3,3-trifluoro-1-propene (HCFO-1233zdE) and 1,1,1,3,3-pentafluoropropane (HFC-245fa) can be recovered at 37 via the pipe 35 in order to be incinerated or purified.

Figure 3A:
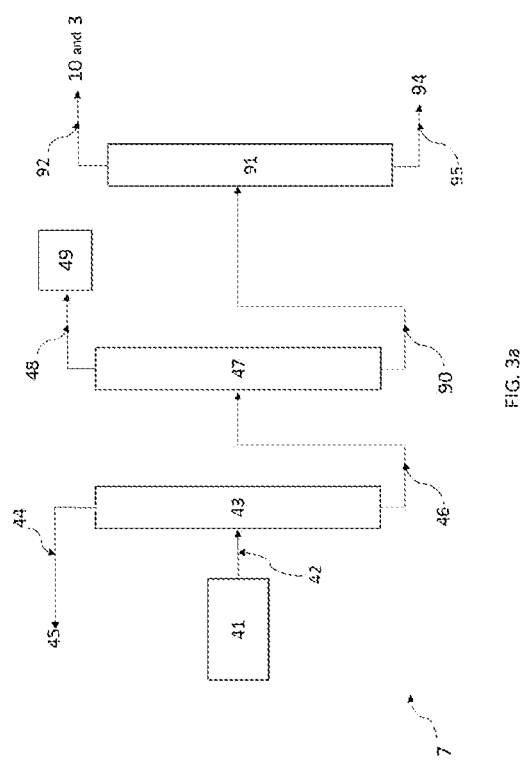

FIG. 3a diagrammatically illustrates, according to a specific embodiment of the present invention, a purification device 7. The gas stream G1 resulting from the distillation column 5 is conveyed into 41 and then to the distillation column 43 via the pipe 42. The stream G1a is recovered at the distillation column 43 top and treated at 45 via the pipe 44. The device 45 can be a device for the purification of the stream G1a. The stream G1b recovered at the distillation column bottom is conveyed to the distillation column 47 via the pipe 46. A stream G1c is recovered at the distillation column top in order to be conveyed to the purification device 49 via the pipe 48. A stream G1d is recovered at the distillation column 47 bottom in order to be conveyed to the distillation column 91 via the pipe 90. The distillation column 91 makes it possible to form a stream G1d' recovered at the distillation column top and a stream G1d" at the distillation column bottom. The stream G1d" can be conveyed to an incinerator 94 via the pipe 95. The stream G1d' can be conveyed to the pipe 10 and the reactor 3 (FIG. 1) via the pipe 92.

Figure 3B:
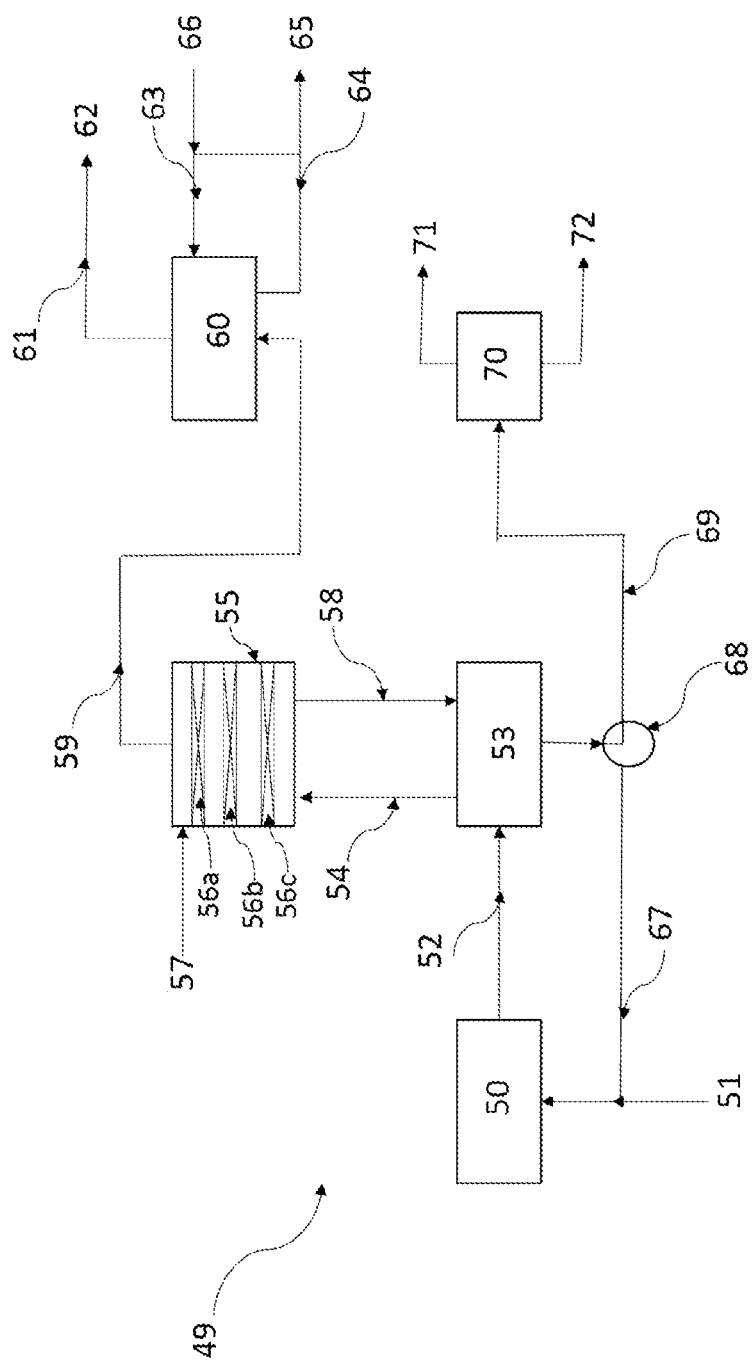
Figure 3C:
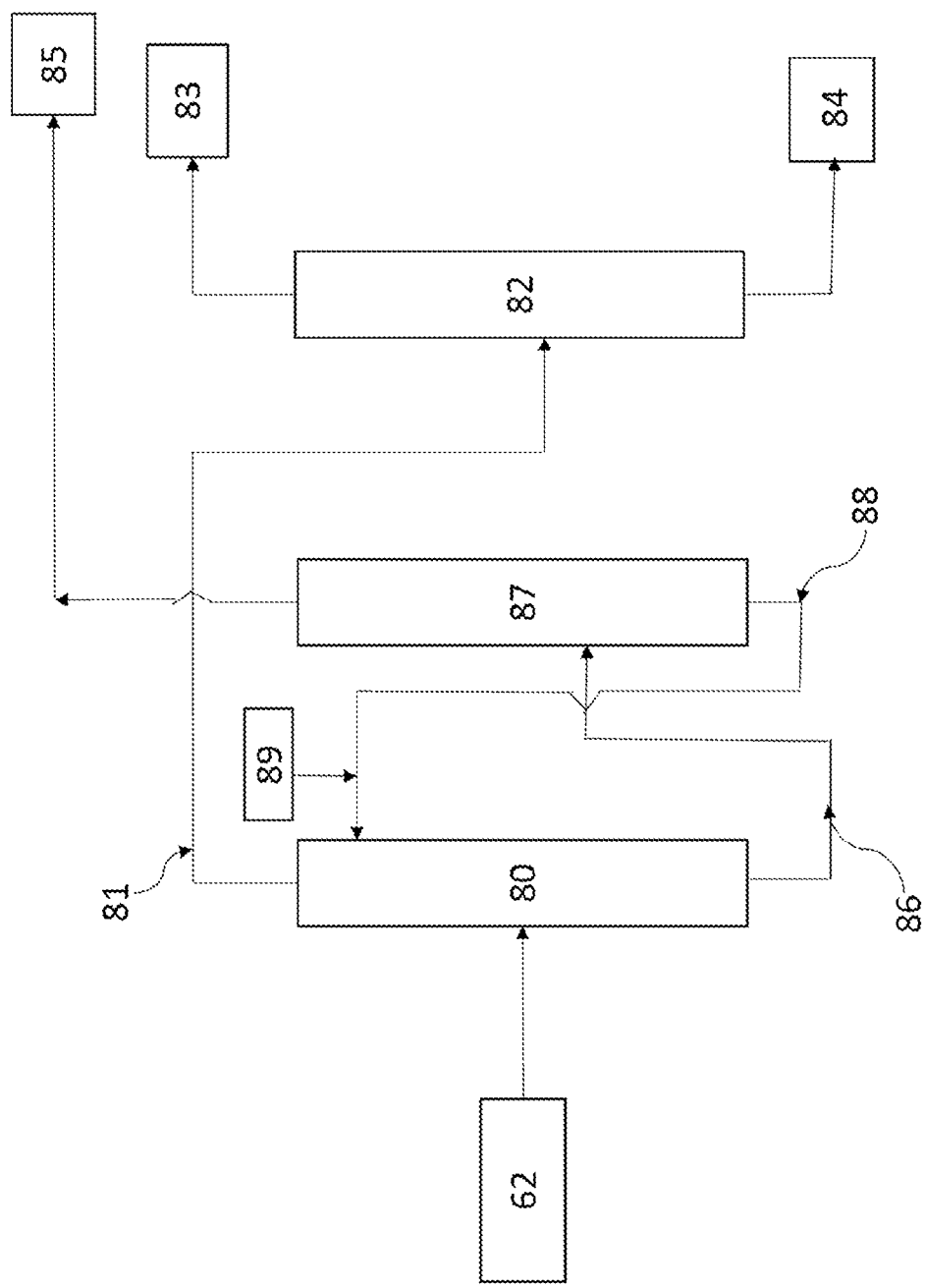

The device 49 is described in detail in FIG. 3b. This comprises a device 50 which makes it possible to bring the stream G1c into contact with a hydrofluoric acid solution 51 having a concentration varying between 65% and 75% by weight. The device 50 can, for example, be a water scrubber. The contacting operation brings about the formation of a two-phase stream G1c' which is conveyed to a storage device 53 via the pipe 52. The gas phase of the two-phase stream G1c' is conveyed via the pipe 54 to the absorption column 55 comprising 3 absorption stages 56a, 56b and 56c. The absorption column 55 is also fed with an aqueous flow 57. In this embodiment, the aqueous flow 57 feeds the absorption column 55 at the absorption column 55 top, that is to say above the three absorption stages 56a-56c. Alternatively, the aqueous flow 57 can feed the absorption column 55 above each of the absorption stages 56a-56c. A gas stream G1c" is extracted at the absorption column 55 top via the pipe 59 in order to feed a neutralization device 60. In addition, at the absorption column 55 bottom, an aqueous hydrofluoric acid solution, corresponding to said stream G1c''', is recycled to the storage device 53 via the pipe 58. The stream G1c'' is neutralized in the neutralization device 60 by an alkaline 20% NaOH solution. The alkaline solution 66 feeds the neutralization device 60 via the pipe 63. The neutralized stream is discharged via the pipe 61 in order to be dried at 62. The neutralized and dried stream corresponds to the stream G1c'''' according to the present process. This stream can optionally be compressed and liquefied at a pressure of at most 8 bara. A spent alkaline solution 65 can be extracted from the neutralization device 60 in order to be either recycled via the pipes 64 and 63 or discharged via the pipe 64 for subsequent treatment. The liquid phase resulting from the mixing of the liquid phase of the two-phase stream and of the stream G1c''' stored in the storage device 53 is conveyed to a distillation column 70 via the pump 68 and the pipe 69 in order to form the stream G2c, recovered at the distillation column 71 top, and the stream G3c, recovered at the distillation column 72 bottom. The pump 68 can also be configured in order to convey the liquid phase resulting from the mixing of the liquid phase of the two-phase stream and of the stream G1c''' stored in the storage device 53 to the device 50 via the pipe 67. The stream G1c'''' obtained at 62 is sent to an extractive distillation column 80 (FIG. 3c). The organic extraction agent 89 is mixed with the stream G1c'''' before entering the extractive distillation column 80. The stream comprising 2,3,3,3-tetrafluoropropene and 1,1,1,2,2-pentafluoropropane is recovered at the distillation column 80 top in order to be conveyed to the distillation column 82 via the pipe 81. The stream comprising 2,3,3,3-tetrafluoropropene and 1,1,1,2,2-pentafluoropropane is separated by the distillation column 82 to form a stream 83 comprising 2,3,3,3-tetrafluoropropene at the distillation column top and a stream 84 comprising 1,1,1,2,2-pentafluoropropane at the distillation column bottom. The stream comprising trans-1,3,3,3-tetrafluoropropene and the organic extraction agent is recovered at the distillation column 80 bottom in order to be conveyed to the distillation column 87 via the pipe 86. A stream 85 comprising trans-1,3,3,3-tetrafluoropropene is recovered at the distillation column top. The organic extraction agent is recovered at the bottom of the distillation column 87 and is recycled to the distillation column 80 via the pipe 88.

The invention claimed is:

1. A process for the production and purification of 2,3,3,3-tetrafluoropropene (HFO-1234yf) carried out starting from a starting composition comprising at least one compound of formula (I) $CH_{(n+2)}(X)_m$—$CH_p(X)_{(n+1)}$—$CX_{(3+p-m)}$, where X independently represents F or Cl; n, m and p are, independently of one another, 0 or 1 with n+m=0 or 1, n+p=0 or 1 and m−p=0 or 1, at least one X being Cl; said process comprising the stages of:
   a) bringing the starting composition into contact, in the presence of a catalyst, with HF under conditions effective in producing a composition A comprising HCl, a part of the unreacted HF, 2,3,3,3-tetrafluoropropene (HFO-1234yf), intermediate products B comprising 2-chloro-3,3,3-trifluoropropene (HCFO-1233xf), 1,1,1,2,2-pentafluoropropane (HFC-245cb) and trans-1,3,3,3-tetrafluoro-1-propene (HFO-1234zeE) and byproducts C comprising trans-1-chloro-3,3,3-trifluoro-1-propene (HCFO-1233zdE), cis-1-chloro-3,3,3-trifluoro-1-propene (HCFO-1233zdZ), cis-1,3,3,3-tetrafluoro-1-propene (HFO-1234zeZ), 1,1,1,3,3-pentafluoropropane (HFC-245fa), 2-chloro-1,1,3,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe), 1,1,1,3,3,3-hexafluoropropane (HFC-236fa) and optionally one or more compounds of formula (II) $C_nH_xF_yCl_z$ in which n=4, 5 or 6, x is an integer from 0 to 6, y is an integer from 4 to 12, z is an integer from 0 to 6, with 2n=x+y+z if w is 1 or 2n−2=x+y+z if w is 2 or 2n+2=x+y+z if w is 0, w being the number of unsaturations in the compound of formula (II) considered;
   b) recovering and purifying said composition A in order to form and recover a gas stream G1 comprising HCl, 2,3,3,3-tetrafluoropropene (HFO-1234yf), a part of the unreacted HF, a part of the intermediate products B and a part of the byproducts C; and a stream, which is liquid, L1 comprising a part of the unreacted HF, a part of the intermediate products B and a part of the byproducts C;
   wherein said gas stream G1 is purified by the following stages:
   b1) distilling the gas stream G1 in order to recover a stream G1a comprising HCl and a stream G1b comprising 2,3,3,3-tetrafluoropropene (HFO-1234yf), a part of the unreacted HF, said a part of the intermediate products B and said a part of the byproducts C;
   b2-1) distilling said stream G1b obtained in stage b1) under conditions effective in forming a gas stream G1c comprising 2,3,3,3-tetrafluoropropene (HFO-1234yf), a portion of said part of said unreacted HF, a portion of said part of the intermediate products B and a liquid stream G1d comprising a portion of said part of the intermediate products B and said part of the byproducts C and a portion of said part of said unreacted HF; and
   b2-2) distilling said stream G1d obtained in stage b2-1) under conditions effective in forming a stream G1d' comprising said portion of said part of the intermediate products B, said portion of said part of said unreacted HF and a portion of said part of the byproducts C comprising cis-1,3,3,3-tetrafluoro-1-propene (HFO-1234zeZ), 1,1,1,3,3,3-hexafluoropropane (HFC-236fa) and a part of trans-1-chloro-3,3,3-trifluoro-1-propene (HCFO-1233zdE) and 1,1,1,3,3-pentafluoropropane (HFC-245fa); and a stream G1d'' comprising a portion of said part of the byproducts C comprising cis-1-chloro-3,3,3-trifluoro-1-propene (HCFO-1233zdZ), 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe), and optionally one or more compounds of formula (II) $C_nH_xF_yCl_z$ in which n=4, 5 or 6, x is an integer from 0 to 6, y is an integer from 4 to 12, z is an integer from 0 to 6, with 2n=x+y+z if w is 1 or 2n−2=x+y+z if w is 2 or 2n+2=x+y+z if w is 0, w being the number of unsaturations in the compound of formula (II) considered.

2. The process as claimed in claim 1, wherein at least 90% of the 1,1,1,2,2-pentafluoropropane and of the trans-1,3,3,3-tetrafluoropropene contained in the stream G1d are recovered in the stream G1d'.

3. The process as claimed in claim 1, wherein the stream G1d' comprises from 60% to 70% by weight of 1,1,1,2,2-pentafluoropropane, from 1% to 5% by weight of trans-1,3,3,3-tetrafluoropropene and from 10% to 15% by weight of 2-chloro-3,3,3-trifluoropropene, based on the total weight of the stream G1d'.

4. The process as claimed in claim 1, wherein at least 85% of the cis-1,3,3,3-tetrafluoro-1-propene (HFO-1234zeZ) and of the 1,1,1,3,3,3-hexafluoropropane (HFC-236fa) contained in the stream G1d are recovered in the stream G1d'.

5. The process as claimed in claim 1, wherein the stream G1d' comprises from 0.1% to 0.5% by weight of cis-1,3,3,3-tetrafluoro-1-propene (HFO-1234zeZ), from 1.0% to 5.0% by weight of 1,1,1,3,3,3-hexafluoropropane (HFC-236fa), from 0.5% to 2.0% by weight of trans-1-chloro-3,3,3-trifluoro-1-propene (HCFO-1233zdE) and from 0.1% to 1.0% by weight of 1,1,1,3,3-pentafluoropropane (HFC-245fa), based on the total weight of the stream G1d'.

6. The process as claimed in claim 5, wherein the stream G1d' further comprises 2-chloro-1,1,1,3,3-pentafluoropropane (HCFC-235da), 1,2-dichloro-3,3,3-trifluoropropene (HCFO-1223xd) and 2-chloro-1,3,3,3-tetrafluoropropene (HCFO-1224xe) in a total content of less than 5% by weight, based on the total weight of G1d'.

7. The process as claimed in claim 1, wherein the stream G1d' is recycled in stage a).

8. The process as claimed in claim 1, further comprising the stages:
b3) bringing the stream G1c into contact with an aqueous hydrofluoric acid solution with a concentration of greater than 40% in order to form a two-phase stream G1c' comprising 2,3,3,3-tetrafluoropropene (HFO-1234yf), hydrofluoric acid, a portion of said part of the intermediate products B and a portion of said part of the byproducts C,
b4) storing said two-phase stream G1c' in a holding tank, said second two-phase stream comprising a liquid phase and a gas phase,
b5) passing the gas phase of said stream G1c' into an absorption column fed countercurrentwise with an aqueous flow in order to form a stream G1c" comprising 2,3,3,3-tetrafluoropropene (HFO-1234yf), a portion of said part of the intermediate products B and a portion of said part of the byproducts C and a stream G1c''' comprising HF;
and optionally the stages:
b6) neutralizing said stream G1c" obtained in stage b5) with an aqueous alkaline solution in order to form a neutralized stream, and
b7) drying said neutralized stream obtained in stage b6) in order to form a neutralized and dried stream G1c''''.

9. The process as claimed in claim 8, wherein the aqueous hydrofluoric acid solution used in stage b3) is at a temperature of between 0 and 30° C. before it is brought into contact with the stream G1c.

10. The process as claimed in claim 8, wherein the process comprises a stage c), subsequent to stage b5) or to stage b7), in which the stream G1c" obtained in stage b5) or the stream G1c'''' obtained in stage b7) comprises 2,3,3,3-tetrafluoropropene (HFO-1234yf), 1,1,1,2,2-pentafluoropropane (HFC-245cb) and trans-1,3,3,3-tetrafluoro-1-propene (HFO-1234zeE); and said stream G1c" or G1c'''' is distilled in order to form a stream G1e' comprising 2,3,3,3-tetrafluoropropene (HFO-1234yf) and 1,1,1,2,2-pentafluoropropane (HFC-245cb) and a stream G1h' comprising trans-1,3,3,3-tetrafluoro-1-propene (HFO-1234zeE).

11. The process as claimed in claim 1, wherein said liquid stream L1 comprises a part of the intermediate products B and all or part of the byproducts C, and a part of the liquid stream L1 is brought to low temperature, in order to form a first phase L1a comprising a part of the unreacted HF and a second phase L1b comprising said intermediate products B and said byproducts C; optionally, said stream G1d formed in stage b2) is mixed with the liquid stream L1 before the latter is brought to low temperature.

12. The process of claim 10, wherein the stream G1c" or G1c'''' is distilled by extractive distillation.

13. The process of claim 12, wherein the stream G1c" or G1c'''' is distilled by extractive distillation by the stages:
c1') bringing said stream G1c" or G1c'''' into contact with an organic extraction agent in order to form a stream G1g', and
c2') extractive distillation of the stream G1g' in order to form the flow G1e' comprising 2,3,3,3-tetrafluoropropene (HFO-1234yf) and 1,1,1,2,2-pentafluoropropane (HFC-245cb), and the stream G1h' comprising trans-1,3,3,3-tetrafluoro-1-propene (HFO-1234zeE) and said organic extraction agent.

14. The process of claim 11, wherein said second phase L1b is distilled in order to recover a stream L1c comprising 1,1,1,2,2-pentafluoropropane (HFC-245cb) and trans-1,3,3,3-tetrafluoro-1-propene (HFO-1234zeE), and a stream L1d comprising 2-chloro-3,3,3-trifluoro-1-propene (HCFO-1233xf), E-1-chloro-3,3,3-trifluoro-1-propene (HCFO-1233zdE) and 1,1,1,3,3-pentafluoropropane (HFC-245fa), and said stream L1c is recycled in stage a).

15. The process of claim 14, wherein said stream L1d is separated by extractive distillation in order to form a flow comprising 2-chloro-3,3,3-trifluoro-1-propene (HCFO-1233xf) and a stream comprising E-1-chloro-3,3,3-trifluoro-1-propene (HCFO-1233zdE) and 1,1,1,3,3-pentafluoropropane (HFC-245fa).

* * * * *